(12) United States Patent
Jiang

(10) Patent No.: US 9,338,382 B2
(45) Date of Patent: May 10, 2016

(54) SYSTEMS, METHODS AND APPARATUS FOR MAKING AND USING EYEGLASSES WITH ADAPTIVE LENS DRIVEN BY GAZE DISTANCE AND LOW POWER GAZE TRACKING

(76) Inventor: Wenyu Jiang, Short Hills, NJ (US)

(*) Notice: Subject to any disclaimer, the term of this patent is extended or adjusted under 35 U.S.C. 154(b) by 212 days.

(21) Appl. No.: 13/118,433

(22) Filed: May 29, 2011

(65) Prior Publication Data
US 2012/0133891 A1  May 31, 2012

Related U.S. Application Data

(60) Provisional application No. 61/349,830, filed on May 29, 2010.

(51) Int. Cl.
*A61B 3/14* (2006.01)
*H04N 5/3745* (2011.01)
*H04N 5/353* (2011.01)
*G02C 7/08* (2006.01)
*G02C 11/00* (2006.01)

(52) U.S. Cl.
CPC .............. *H04N 5/3745* (2013.01); *G02C 7/083* (2013.01); *G02C 11/10* (2013.01); *H04N 5/3535* (2013.01); *G02C 2202/24* (2013.01)

(58) Field of Classification Search
USPC .......... 351/200, 205–210, 220–222, 245–247
See application file for complete search history.

(56) References Cited

U.S. PATENT DOCUMENTS

| 5,741,048 | A   | * | 4/1998  | Eccleston ................... 303/7 |
| 7,023,594 | B2  |   | 4/2006  | Blum et al. |
| 7,517,083 | B2  |   | 4/2009  | Blum et al. |
| 7,956,313 | B2  | * | 6/2011  | Sato et al. ................ 250/208.1 |
| 2006/0221221 | A1 | * | 10/2006 | Furukawa et al. .......... 348/302 |
| 2008/0122953 | A1 | * | 5/2008  | Wakahara et al. .......... 348/241 |
| 2008/0203277 | A1 |   | 8/2008  | Warszauer et al. |
| 2010/0114540 | A1 |   | 5/2010  | Shinohara et al. |
| 2010/0116999 | A1 |   | 5/2010  | Tumer et al. |

FOREIGN PATENT DOCUMENTS

JP  2002-217369  *  8/2002  ............ H01L 27/04
WO  97/43006  11/1997

OTHER PUBLICATIONS

Dongsoo Kim et al., "A 200 us Processing Time Smart Image Sensor for an Eye Tracker Using Pixel-Level Analog Image Processing", IEEE Journal of Solid-State Circuits, vol. 44, No. 9, pp. 2581-2590, Sep. 2009.

(Continued)

*Primary Examiner* — Scott J Sugarman
*Assistant Examiner* — Brandi Thomas
(74) *Attorney, Agent, or Firm* — Greenberg Traurig, LLP

(57) ABSTRACT

Described is an electro-optical apparatus and method for correcting myopia that includes at least one adaptive lens, a power source, and an eye tracker. The eye tracker includes an image sensor and a processor operatively connected to the adaptive lens and the image sensor. The processor is configured to receive electrical signals from the image sensor and to control the correction power of the adaptive lens to correct myopia, with the correction power dependent on a user's gaze distance and myopia prescription strength. A lower-power-consumption method of eye glint tracking is further described.

18 Claims, 12 Drawing Sheets

(56) References Cited

OTHER PUBLICATIONS

John Michael Morookian, "Ambient-Light-Canceling Camera Using Subtraction of Frames"; NASA Tech Briefs, May 2004.

Sheng-Wen Shih et al., "A Calibration-Free Gaze Tracking Technique", International Conference on Pattern Recognition, pp. 201-204, 2000.

Dan Witzner Hansen et al., "In the Eye of the Beholder: A Survey of Models for Eyes and Gaze", IEEE Transactions on Pattern Analysis and Machine Intelligence, vol. 32, No. 3, pp. 478-500, Mar. 2010.

Tony (SelectSpecs), "Electricfying Vision—Lenses with Artificial Intelligence from PixelOptics"; SelectSpecs.com, http://www.selectspecs.com/blog/electrifying-vision/, pp. 1-4, Feb. 12, 2010.

K. J. Kabza, "Liquid Lens Innovations; Takes Initial Form in Camera Phones", http://www.digitalcamerainfo.com/content/Liquid-Lens-Innovations-Takes-Initial-Form-in-Camera-Phones-.htm, pp. 1-9, Feb. 9, 2006.

B. Berge, "Liquid Lens Technology: Principle of Electrowetting Based Lenses and Applications to Imaging", Proceedings of the MEMS 2005 Conference, Jan. 30-Feb. 3, 2005, Varioptic.

"Mold LED Lamp L880series: Infrared LED Lamp", http://www.tech-led.com/data/L-880-AU.pdf, Marubeni America Corporation.

Wayne Storr, "Priority Encoder", Electronics-Tutorials.ws, http://www.electronics-tutorials.ws/combination/comb_4.html, pp. 4-8, May 2011.

Duncan Adams, "Developer: Electronic eyeware in sight", The Roanoke Times, Jan. 6, 2010.

Jun Ohta, "Smart CMOS Image Sensors and Applications", Fundamentals of CMOS Image Sensors, 2008, pp. 28-43, CRC Press.

"Standard-Line Near Infra-red Bandpass Filter Listing", NIR Filters, Cheshire Optical.

Hong Hua et al., "Video-based eyetracking methods and alogorithms in head-mounted displays", May 16, 2006, vol. 14, No. 10, Optics Express.

\* cited by examiner

SYSTEMS, METHODS AND APPARATUS FOR MAKING AND USING EYEGLASSES WITH ADAPTIVE LENS DRIVEN BY GAZE DISTANCE AND LOW POWER GAZE TRACKING

PRIORITY CLAIM

This application claims the benefit of U.S. Provisional Patent Application No. 61/349,830 filed May 29, 2010, the entire disclosure of which is incorporated herein by reference.

FIELD OF THE INVENTION

This application relates in general to the fields of optics and electronics, and in particular to devices and methods for controlling adaptive lenses in eyeglasses and other optical devices.

BACKGROUND

Modern eyeglasses are customarily used to correct the vision of patients or users, with myopia being the most common and prevalent symptom amongst patients. Hereinafter the terms "patient" and "user" are used interchangeably. A main cause of myopia is the inability of the eye's own crystalline lens (hereinafter the "eye lens") to revert to a lower optical power (or thinner shape) plausibly due to the overly long duration of focusing on near objects which may require a higher optical power (a thicker shape).

When a patient is first diagnosed with myopia, typically at a young age, his or her corrective prescription is often at a relatively low optical power: e.g., −1.5 diopter, which means that the patient can view objects clearly at up to 1/1.5 m=0.667 m=66.7 cm. When the patient, say a student, wears eyeglasses to read a blackboard in a classroom setting, he or she can see the text without much effort. However, when the patient attempts to read a textbook or write notes in a notebook, and the textbook or notebook is at a close distance of 30 cm from the patient's eyes, then utilizing optical equations the virtual image formed by the eyeglasses may be at 1/(−1.5−1/0.3) m=−0.206 m=−20.6 cm. In other words, it is as if the patient is reading or writing at a distance of 20.6 cm instead of 30 cm. Therefore, the patient has to repeatedly change his or her focus between reading/writing and looking at the blackboard, which may be exhausting, and the accommodation (or change of focus) at a near distance may be stronger or greater than if the patient does not wear any eyeglasses. This constant change of focus forces the patient's eye lens(es) into an even higher optical power than before, and after a prolonged period of reading/writing, the eye lens(es) may lose the ability to revert to even the original −1.5 diopter, because during reading/writing the patient effectively focuses at 20.6 cm instead of 66.7 cm, and this may present unhealthy wearing of the eyes. Gradually, a pair of higher prescription eyeglasses would be required by the patient, which may in turn drive the patient's eye lens(es) into unnecessarily high optical powers. Eventually, the mechanical property of the eye lens(es) (which may vary from person to person) may impose a limit on how much the lens(es) may be compressed, thereby stabilizing the user's prescription strength. However, the prescription strength may be stabilized at the great cost of requiring a much higher prescription than the original prescription.

Bifocal, multi-focal and progressive lenses have been used for reading purposes, intended for users with presbyopia (e.g., the inability to focus at near distance when wearing normal prescription eyeglasses, which usually begins to affect vision in middle age). Bifocals, multi-focals and progressive lenses are limited in that they require patients to look down to use the lower prescription part of the lens, which is often inconvenient. Furthermore, eye care professionals seem to believe that these types of lenses are meant for presbyopia patients instead of myopia patients.

PixelOptics, Inc. of Roanoke, Va., has released a type of eyeglasses using adaptive lenses that change focal length depending on viewing distance, however their eyeglasses are intended strictly for presbyopia users and/or older patients, whereas the present disclosure addresses myopia for patients of all ages. Furthermore, the present disclosure is distinguishable from the PixelOptics adaptive lens in that given a prescription that the patient has no problem using to view objects at close distance, the focal length is adapted accordingly, whereas the PixelOptics eyeglasses are not known to perform such adaptation. Furthermore, the PixelOptics eyeglasses vaguely perform eye tracking, but not the specific eye tracking as disclosed by the present disclosure. U.S. Pat. No. 7,517,083, assigned to PixelOptics, potentially suggests the use of eye or gaze tracking to control the focal length of adaptive lens. However, the patent does not provide sufficient detail on implementing eye tracking, and merely mentions the use of LEDs and image sensors for detecting the edges of pupils, which suggests pupil-based eye tracking, but no details are provided to implement pupil tracking with a small form factor and in addition, inter-pupillary distances are suggested in the patent for determining viewing distance. However, the inter-pupillary distances are not completely accurate when a patient looks sideways whereas using a "line-of-sight" intersection approach to calculate the distance is generally more accurate. Furthermore, the concept of inter-pupillary distance tacitly assumes that there is one gaze distance from both eyes, but that is true only when the user looks straight ahead (e.g., up or down is acceptable). For instance, when looking to the left side, especially for close objects, the left eye will be closer to that object than the right eye. The line-of-sight intersection approach does not encounter this problem.

A range finder method is also discussed in U.S. Pat. No. 7,517,083, which generally finds the closest straight-ahead object, which is not the same as finding the gaze distance. According to various PixelOptics literature and press releases, its newly released eyeglasses may be capable of "knowing where you're looking at."

Furthermore, U.S. Pat. No. 7,517,083 mentions using a tracking system to "calculate the range of near point focus in order to correct for one's accommodative and convergence near or intermediate range focusing needs", which is a vague description that seems to apply strictly to the focusing needs of presbyopia users and not the focusing needs of myopia users.

In addition, the type of eye tracking discussed in U.S. Pat. No. 7,517,083 are most often utilized for correcting non-conventional aberrations in vision such as, for example, astigmatism, instead of more commonly occurring aberrations such as, for example, myopia. In practice, eye or gaze tracking is complex and is a concept that should be discussed in clearer and fuller detail, especially in a small form factor context.

Eye or gaze tracking itself is a complicated subject that has been around for decades and still is non-trivial to implement. The technology surrounding eye or gaze tracking has advanced significantly, enabling optical manufacturers to spend large amounts of money to make and produce commercial trackers (or Head-Mounted Eye Trackers), which may be sold for upwards of thousands of dollars. Existing research suggests that Head-Mounted Eye trackers are relatively bulky and consume significant amounts of energy, perhaps hundreds of mW (milli-Watts).

One 2009 paper, entitled "A 200 µs is Processing Time Smart Image Sensor for an Eye Tracker Using Pixel-Level Analog Image Processing" describes a Smart CMOS image sensor that directly implements eye tracking at a 100 mW peak consumption. See Dongsoo Kim, Gunhee Han (Dept. of Electrical Engineering, Yonsei University, Seoul, Korea), *A 200 µs Processing Time Smart Image Sensor for an Eye Tracker Using Pixel-Level Analog Image Processing*, 44 IEEE JOURNAL OF SOLID-STATE CIRCUITS 2581-90 (September 2009) (Volume 44, Issue 9). The paper discusses the current state-of-the-art of low-power design for eye trackers and shows how attempting to develop a sub-mW consumption remains a key design goal. However, the paper does not achieve sub-mW consumption. The design discussed in the above paper supports 5000 trackings per second. Thus, if the number of trackings were reduced to just 50 trackings per second, then the total power consumption may be able to be reduced to 1 mW.

One 2004 paper, entitled "Ambient-Light-Canceling Camera Using Subtraction of Frames", proposes double exposures with time modulated (On/Off) controlled lighting and then subtraction to cancel ambient (background) light interference. See NASA's Jet Propulsion Laboratory (Pasadena, Calif.), *Ambient-Light-Canceling Camera Using Subtraction of Frames*, NASA TECH BRIEFS, NPO-30875 (May 2004), available at: http://findarticles.com/p/articles/mi_qa3957/is_200405/ai_n9457885/?tag=content;col1. The subtraction may be done in software instead of hardware.

In addition, U.S. Patent Publication No. 2008/0203277 by Zamir Recognition Systems, a company located in both Knoxville, Tenn. and Jerusalem, Israel, describes an approach similar to the above-mentioned approach of the above-mentioned 2004 NASA Tech Brief, but in hardware. Two approaches are outlined in the above-mentioned patent Publication: (i) one approach using a time modulated (On/Off) controlled light like in the above-mentioned 2004 NASA Tech Brief and (ii) the other approach using frequency modulation (similar to AM/FM radio tuning) to be more receptive to certain controlled frequencies. The frequency modulation approach may be more complex to implement compared to the time modulated approach. Each pixel in the camera has a capacitor. The time-modulated approach may use charging and discharging the capacitor of each pixel in one array of pixels, or charging two arrays of pixels, and then performing subtraction.

FIG. 3 of U.S. Patent Publication No. 2008/0203277 seems to exhibit a static electricity hazard, which is logically inconsistent with the overall design of a charging and discharging approach. Furthermore, for the time-modulation approach with two pixel arrays, the subtraction of signals in hardware or software is suggested. Even for hardware subtraction, U.S. Patent Publication No. 2008/0203277 appears to suggest that prior art methods are used, e.g., a differential operational amplifier is typically used as a subtraction module in the analog domain, and an arithmetic unit after digitization is typically used as a subtraction module in the digital domain.

SUMMARY OF INVENTION

Sometimes a patient at an early stage of myopia may temporarily recover the ability to view objects at a far away distance if they actually view far away objects for an extended period of time. This may be presumably achieved by the muscles relaxing and letting the eye lens revert back to a thinner shape on its own. Therefore, if eyeglasses are designed in a way that allows the muscles to relax as much as possible while still maintaining visual acuity and sufficient vision correction, the user may be able to potentially reduce his or her myopia symptoms and/or prevent further increases in prescription strength. This may be achieved by using a lens having adaptive focal length. If a patient's prescription strength for far viewing is known, then at a maximum level of eye relaxation, such eyeglasses may be able to provide only as much correction as necessary to provide just enough vision correction or vision correction at adequate and satisfactory levels. This way, the patient may be able to maintain his or her original prescription rather than increasing it unnecessarily. It may also even be possible to reduce the corrective power of a set of lenses by a small amount so that the eye may be given the urge to focus (towards a far distance), thereby possibly reversing the effect of myopia.

The above-described approach can be implemented using adaptive lens technologies (e.g., electrowetting, liquid crystal, liquid lens with fluid injection, etc.) in combination with a means for determining "gaze distance" or exactly how far away a patient is focusing when looking at an object at a distance. Gaze distance is not necessarily the straight-ahead distance to the closest front object, because one may be able to look sideways, e.g., glimpsing.

A novel observation regarding gaze distance is that it depends on the line of sight of each eye and may be equal to the intersecting distance of those two lines of sight, due to the way human eyes perceive stereo vision.

One embodiment of the above-described approach uses methods that advantageously utilize glint tracking. In one embodiment, a method is provided that has the advantage of being calibration-free when combined with prior-art methods. In one embodiment, a method is provided to perform very low power glint tracking using Smart CMOS image sensors by modifying the Active Pixel Sensor (APS) element.

In one embodiment, the present disclosure may utilize one array of pixels but two capacitors aptly placed at the source and the gate of a MOSFET transistor, which thus facilitates glint detection. This approach is distinguishable from the above-described time-modulation approach of U.S. Patent Publication No. 2008/0203277 and may also use fewer pixels. Also, the above-described time and frequency modulation approaches of U.S. Patent Publication No. 2008/0203277 are designed more for general image capture and not for glint detection. In comparison, the two-capacitor design of the present disclosure is a new way to perform essentially subtraction but with glint-only detection and at low power, instead of detecting pixels at any light intensity with high power.

In one embodiment, the present disclosure provides an easy-to-implement, low-power-consumption (sub-mW) viewing device that can be manufactured in an economic manner.

In one embodiment, a new type of eyeglasses is provided that reduce the amount of accommodation required for users with myopia at all distance ranges of viewing, thereby reducing eye strain and hopefully slowing down, stabilizing or even reversing the progression of myopia. The eyeglasses may adapt the optical power of its lenses, such that a reduced amount of accommodation is required of myopia users compared to wearing full prescription strength glasses. The reduced accommodation amount may be less than full but still positive when compared to full prescription strength glasses. This may help maintain an implicit relationship between convergence and accommodation that the brain assumes, so that when a patient takes off his or her glasses, he/she may still be able to see naturally because the brain knows it has to refocus the eye lenses for different distances. Alternatively, the reduced accommodation amount may be slightly more than full, where the user does not see 100% clearly, and is tempted to focus towards a far distance, thereby helping the eye lens (es) to revert to a thinner shape (and lower power) and potentially reverse the progression of myopia. The eyeglasses may need to know the viewing distance, which is determined by gaze distance. The eye or gaze tracker provided by the present disclosure is based on tracking eye glints from infrared LED illumination. The eye or gaze tracker may be easy to implement, making it suitable for embedded use (in eyeglasses) and facilitates calibration-free use when combined with prior-art methods.

In one embodiment, a gaze tracker for use in eyeglasses not only has to be easy to implement but also may have a very low power consumption. A design goal is to have sub-mW power consumption, preferably during active periods of tracking. The actual design in accordance with the present disclosure may be used to modify the Active Pixel Sensor (APS) in a Smart CMOS image sensor, and may consume noticeable power only when a pixel is turned on, and the pixel may be turned on only if the incident light is strong enough (e.g., a glint is captured on the pixel). This approach supports a very low power design, possibly less than 0.1 mW during active periods. Two methods are described, with one having a simpler implementation, and the other being more complex and having a higher immunity to background light interference. In contrast to the prior approaches, particularly that of the Kim & Han paper discussed above, the presently disclosed systems and methods provide a design that can support sub-mW power consumption even during active periods. For example, if a 1 µA to current limiting transistor is used as a load, and a 3V power supply is also used, then a glint detection circuit (as part of a glint-based gaze tracker) in the design of the present disclosure may only consume on the order of 30 µW during active periods if, for example, 10 glint pixels are expected in an image captured by the gaze tracker camera. Also, the eye tracker discussed by the above 2009 paper tracks merely the center of a pupil, whereas the present disclosure tracks the glint, which may be only one pixel or a small cluster of pixels, thereby making the circuit design much simpler and more robust.

In one embodiment, novel embodiments of eyeglasses are provided that may adjust their optical power based on gaze distance, so as to reduce the amount of accommodation required of users with myopia when such users are looking at a near distance, for example. The eyeglasses allow the user to relax his or her eyes as much as possible whether the user looks at far or nearby objects, which may help in slowing down and possibly reversing the progression of myopia. The optical adjustments performed by the eyeglasses may be enabled by using, for example, adaptive lens, and the adaptive lens may in turn be implemented in several ways: e.g., liquid electrowetting, liquid crystal and liquid lens with fluid injection.

In one embodiment, a method for performing gaze tracking for gaze distance estimation is provided. The method may require just glint tracking, which may be simpler to implement. The method may also be made calibration-free by combining with it or its steps prior art auto-calibration methods or steps from such prior-art auto-calibration methods. The method may also facilitate a low complexity implementation, with, for example, the usage of 1 LED illumination and two or more cameras.

In one embodiment, an ultra low power (e.g., sub mW or milli-Watt) method to implement glint tracking in cameras by using, for example, Smart CMOS (Complimentary Metal Oxide Semiconductor) image sensors which may also have modified Active Pixel Sensors (APS) is provided. The modified APS may consume very lower power because a pixel is turned on (and consuming noticeable power) only if it is potentially a glint pixel (e.g., with strong enough light intensity). A near-infrared narrow-band filter may be utilized as a preferred approach to improve the immunity to background light interference. Exposure time may also be reduced compared to the rate of normal image capture, which may facilitate both glint-only detection and low power consumption for LED illumination. In other words, the LED may not have to be "on" all the time. In one embodiment, a variant of the above described method may also be provided that may support stronger immunity to background light interference by using two capacitors in the APS for two exposures, and a modified voltage supply to interface the output signal of the APS. In one embodiment, a variant of the above described method may also be provided that may achieve a similar goal of the previously described method (e.g., stronger immunity to background light) without, however, the use of either two capacitors and/or a modified voltage supply.

BRIEF DESCRIPTION OF THE DRAWINGS

The embodiments are illustrated by way of example and not limitation in the figures of the accompanying drawings in which like references indicate similar elements.

DETAILED DESCRIPTION OF THE PRESENT DISCLOSURE AND FIGURES

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Figure 1:
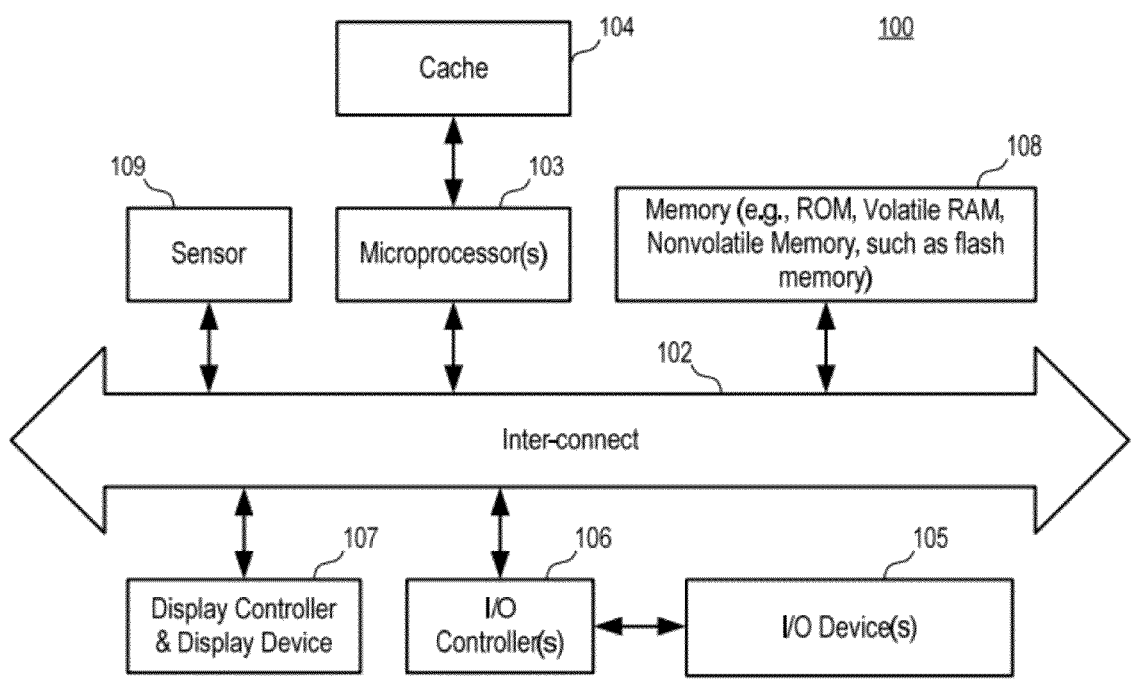
FIG. 1 shows an example of a hardware apparatus used in tandem with eyeglasses having adaptive lenses driven by gaze distance and low power gaze tracking according to an embodiment of the present disclosure.

FIG. 1 shows an example of a hardware apparatus used in tandem with eyeglasses having adaptive lens driven by gaze distance and low power gaze tracking according to an embodiment of the present disclosure. While FIG. 1 illustrates various components of an embedded device, it is not intended to represent any particular architecture or manner of interconnecting the components. Some embodiments may use other systems that have fewer or more components than those shown in FIG. 1.

In FIG. 1, the data processing system 100 includes an inter-connect 102 (e.g., bus and system core logic), which interconnects a microprocessor(s) 103 and memory 108. The microprocessor 103 is coupled to cache memory 104 in the example of FIG. 1.

The inter-connect 102 interconnects the microprocessor(s) 103 and the memory 108 together and also interconnects them to a display controller, display device 107, the sensor 109 and to peripheral devices such as input/output (I/O) devices 105 through an input/output controller(s) 106.

The sensor 109 may include a CMOS or CCD image sensor. The sensor 109 may further include, for example, an accelerometer to determine the orientation of the device and/or to detect the shaking of the device, or as another example, audio recording equipment to record sound near the user, or as yet another example, optical devices to measure, observer or record visual data.

Typical I/O devices include mice, keyboards, modems, network interfaces, printers, scanners, video cameras, touch pads, microphones and other devices which are well known in the art. In some embodiments, when the data processing system is a server system, some of the I/O devices, such as printer, scanner, mice, and/or keyboards, are optional.

The inter-connect 102 may include one or more buses connected to one another through various bridges, controllers and/or adapters. In one embodiment the I/O controller 106 includes a USB (Universal Serial Bus) adapter for controlling USB peripherals, and/or an IEEE-1394 bus adapter for controlling IEEE-1394 peripherals.

The memory 108 may include ROM (Read Only Memory), volatile RAM (Random Access Memory), and non-volatile memory, such as hard drive, flash memory, etc.

Adaptive Lens Technology

As mentioned above, patients with myopia suffer from the fact that when looking at near objects, their eye lens(es) have to accommodate much more when wearing full prescription eyeglasses compared to when not wearing eyeglasses, thereby forcing their eye lens(es) to remain at an optical power unnecessarily higher than before. With prolonged use, the eye lens(es) will probably be unable to revert to their original shape, thus increasing the patient's myopia prescription. Even without eyeglasses, reading at a close distance for too long is plausibly not a good eye habit. With eyeglasses, the problem becomes exacerbated much further.

Therefore, a new type of eyeglasses is provided that adjusts its focal length or optical power so as to reduce the amount of accommodation required of a patient with myopia when looking at objects of most practical distances. A key requirement of such an adaptive lens for use in eye glasses is compactness, and that requirement usually rules out the multi-focal combination lens(es) used in most cameras, which are usually too large and require moving parts. Recent developments in optical technology, however, have made adaptive lens a reality. Several types of adaptive lens designs exist, such as, for example, liquid lens with electrowetting, liquid crystal lens, and lens with fluid injections. With regard to electrowetting, see Liquid Lens Technology: Principle of Electrowetting based Lenses and Applications to Imaging, B. Berge, Varioptic, Proceedings of the MEMS 2005 conference, Jan. 30-Feb. 3 2005-02-05, the disclosure of which is incorporated herein by reference. With regard to liquid crystal lenses, see U.S. Pat. No. 7,517,083, the disclosure of which is incorporated herein by reference. With regard to lenses with fluid injections, see Liquid Lens Innovations; Takes Initial Form in Camera Phones, K. J. Kabza, Feb. 9, 2006, the disclosure of which is incorporated herein by reference. As long as a given adaptive lens technology meets certain requirements in metrics such as form factor, range of focal lengths and power consumption, they will be suitable for use with the eyeglasses provided by the present disclosure. Furthermore, an adaptive lens may be combined with a fixed power lens (e.g., sticking two lenses together) in order to achieve the desired optical range and/or improve cost effectiveness.

Modes of Accommodation Reduction

Figure 2:
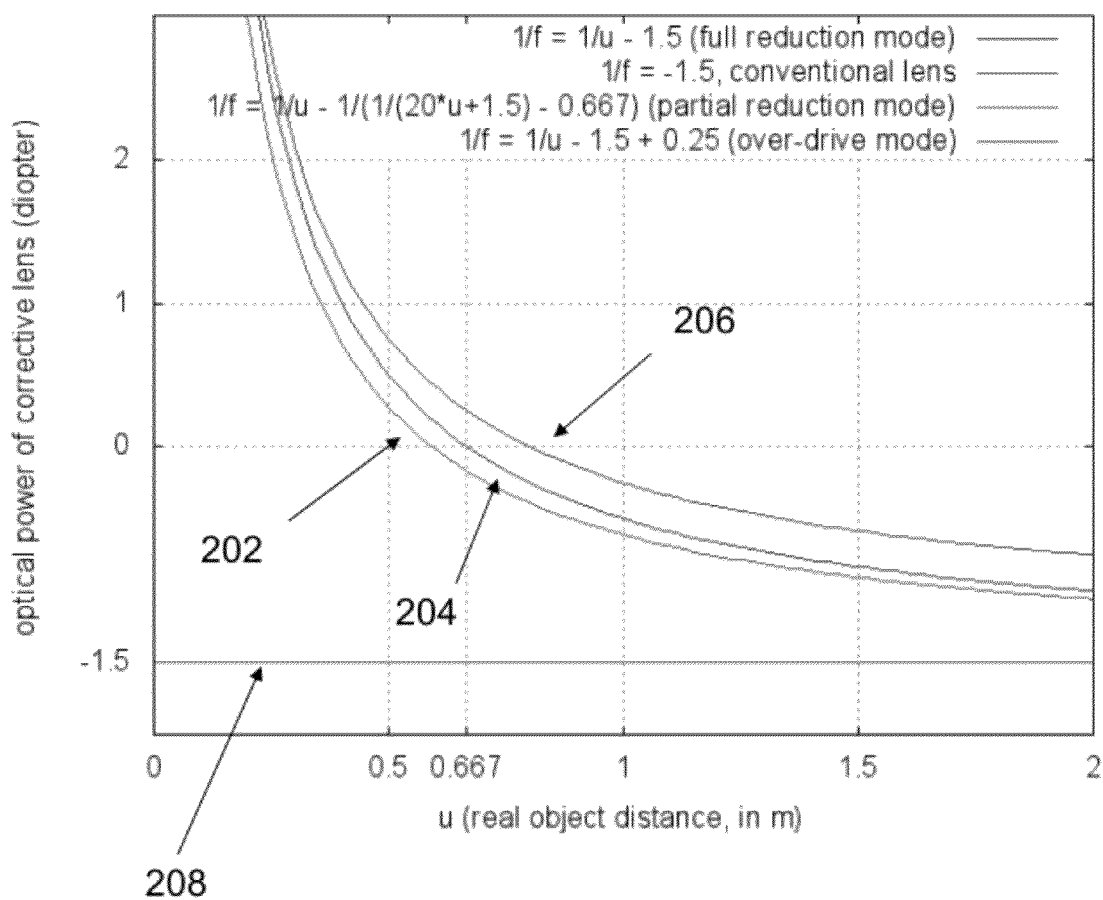
FIG. 2 shows a graph of different accommodation reduction modes, according to an embodiment of the present disclosure.

FIG. 2 shows a graph of different accommodation reduction modes, according to an embodiment of the present disclosure. Graph 200 includes partial reduction mode plot 202, full reduction mode plot 204, overdrive reduction mode plot 206, and conventional lens plot 208 where the y-axis is optical power of corrective lens in diopters and the x-axis is the real object distance in meters, represented by a variable "u".

The level of reduction in the amount of required accommodation can have several modes. In the first mode, full reduction mode—which is represented by full reduction mode plot 204—the reduction amount is full, e.g., the patient's eye lens(es) are completely relaxed and never have to accommodate to looking at far or near objects. For example, if a patient's myopia prescription is −1.5 diopter, with full reduction mode, the adaptive lens(es) in the eyeglasses may always form a virtual image of the object of interest at a distance of 1/1.5=0.667 m=66.7 cm. Note that if the object of interest is at a real distance shorter than 66.7 cm, the adaptive lens(es) must change from a concave shape to a convex shape, so that the virtual image distance is still at 66.7 cm. Therefore, in the full reduction mode, the eye lens(es) are always maintained at their thinnest shape and lowest optical power (as far as the current myopia prescription is concerned), and this may help the patient slow down or prevent further progression of myopia. Full reduction mode is again illustrated by full reduction mode plot 204. Note that for full reduction mode plot 204, when real object distance u=66.7 cm (x-axis), the adaptive lens in full reduction mode will have an optical power of zero (y-axis), because a user with −1.5 diopter prescription can see clearly without eyeglasses at up to 66.7 cm. If u reduces even further, the adaptive lens will change from negative to positive optical power.

In the second mode, partial reduction mode—which is represented by partial reduction mode plot 202—the reduction is less than in full mode, but the reduction amount is still positive compared to wearing full prescription eyeglasses. One may set a lower limit on the virtual image distance. For example, if the user prescription is −1.5 diopter, and if we set the said lower limit to 30 cm, then the adaptive lens(es) will ensure that no matter how close the object of interest is, the virtual image is formed at 30 cm or farther. The exact mapping between real object distance and virtual image distance (which controls the optical power of the adaptive lens) may take on any function form, as long as the virtual image distance is a non-increasing function of real object distance and it starts at $|f_0|$ where $f_0$ is the focal length of the adaptive lens at full prescription, e.g., the inverse of myopia prescription in diopters. In practical use, we may also specify a low limit when real object distance is no shorter than a preset practical lower threshold, e.g., 10 cm. Alternatively, we can directly specify the optical power of an adaptive lens with respect to real object distance, and such function in the partial reduction mode would generally be a non-increasing function between the flat line 1/f0, and the curve 1/f=1/u+1/f0, where u is the real object distance (x-axis). Note that although this function should preferably be non-increasing with respect to the real object distance and the function of virtual image distance should be non-decreasing with respect to the real object distance, minor modifications to these function to break their non-increasing or non-decreasing properties should be considered trivial imitations. Partial reduction mode plot 202 illustrates partial reduction mode, where the virtual image distance v is defined as a function of u as: v=1/(20*u+1.5)−0.667. The term −0.667 specifies a maximum value of v, and 1.5 (diopter) is used to ensure that for any u>0, the condition v<0 is satisfied (because the virtual image is on the same side as the corrective lens). However, these are just illustrative examples and other functions may also be used.

The partial reduction mode may also be important in maintaining an implicit relationship between convergence and the accommodation assumed by the brain. When we look at a close object, we have a stronger convergence because our eyes rotate inward to maintain proper stereoscopic vision. Normally, for people with good vision (and even those with myopia but wearing conventional eyeglasses), our eye lenses accommodate further (e.g., convert to a higher optical power) to focus at near objects. In full reduction mode, however, the eye lens(es) never have to change focus. Although it may be beneficial in the sense that the eye lens(es) are always in fully relaxed mode, the implicit convergence/accommodation relationship is no longer present. With prolonged use, the brain may lose or significantly weaken that implicit relationship, and when the patient takes off his or her eyeglasses, he/she may find it hard to look at objects of different distances clearly, even when the objects are within his/her clear vision distance, because at different distances the eyes have different convergence, but the brain may not trigger the urge to change focus. Therefore, partial reduction mode addresses this potential problem. On the other hand, myopia users wearing conventional eyeglasses already have a different convergence/accommodation relationship than when not wearing eyeglasses, so it is plausible that any monotonic relationship/mapping may work, as long as there exists one such relationship/mapping with non-negligible (as far as the brain is concerned) ranges in accommodation. This suggests there is relatively high flexibility in choosing the function of virtual image distance or optical power with respect to real object distance, which controls such mapping.

In the third mode of overdrive reduction mode—which is represented by overdrive reduction mode plot 206—the reduction is slightly more than the full amount, so that the eye does not see the object of interest 100% clearly, with the intention that the eye lens(es) may be urged to focus towards a far distance in order to see clearly. If such an urge is successfully triggered, the progression of myopia may even be reversed. As can be seen by the overdrive reduction mode plot 206, the corrective power is short by 0.25 diopter for all distances. However, other functions may also be used.

In any of the above modes, ergonomic features may be added to promote good eye habits and health. For example, if the real object distance is shorter than a pre-determined threshold and optionally dwells longer than a pre-determined amount of time, the eyeglasses may beep, for example, to remind the user that he/she is looking at objects too closely.

For hyperopia users, e.g., those who can see clearly at a far distance but have difficulty focusing at near objects, similar but slightly different modes can be used. For example, the adaptive lens(es) may adjust their optical power such that the image is effectively always formed at the nearest clear vision distance, say 50 cm for a prescription of +2 diopter. However, this will keep the user always in near vision focus even when looking at far objects, which may strain the eyes. Alternatively, the adaptive lens(es) may provide a positive power so that when viewing objects closer than the nearest clear vision distance, the image is effectively formed at the nearest clear vision distance, but when viewing objects farther than the nearest clear vision distance, the adaptive lens(es) will have zero power so that the patient uses his/her natural vision and focus. As in the case of myopia, the effective image distance may be kept static, or may change slightly over different real object distances so that the brain retains some implicit relationship between convergence and accommodation.

The conventional lens plot 208 shows a constant optical power (here, shown as −1.5 diopter) that is exhibited by a conventional lens, for example.

Gaze Distance and Gaze Tracking

Determining the real object distance, e.g., the distance of the object of interest or the viewing distance, is not a trivial task. It is not always the straight-ahead distance to the closest front object, because a user can always look sideways, e.g., by glimpsing. Therefore, if one uses a camera having an auto-focus capability (which usually works by tuning to a focal length that produces the sharpest edges within a specified region such as the straight-ahead front) and mounts it on the front of the eyeglasses, it will not work when the user glimpses. In the worst case scenario, when there are a lot of objects at different distances within a small view angle, the viewing distance can change significantly when the glimpse angle changes slightly. Similarly, a range finder device that emits a small pulse of light or ultrasound wave and monitors timing of reflections to determine the viewing distance may have the same problem.

Human eyes may perceive vision in a stereoscopic manner. The eyes have highest visual acuity in the fovea region of the retina, and to perceive high details of an object, both eyes usually may rotate in a way so that the object forms an image in the fovea region. At the same time, in order to avoid double vision when focusing on the object of interest, the rotations of the eyes have to be very precise such that both fovea images of the object overlap nearly perfectly in stereoscopic vision. Therefore, viewing distance may be determined by the lines-of-sight of both eyes. The two lines may intersect at the object of interest due to this observed requirement of stereoscopic vision. The intersection point represents the 3D coordinate of the object of interest (or more precisely, the part of the object that the user is focusing on). In practice, both measurement errors and non-perfect stereoscopic eye alignment may cause the two detected lines-of-sight not to intersect. To deal with these errors, some form of approximations may be used. For example, instead of being modeled as abstract thin lines, both lines-of-sight may be extended to a beam either with a small radius, or with a small solid angle (which covers more area as it goes towards far distances), and the center of the resulting intersecting region (e.g., its geometric centroid) is considered the 3D coordinate of the object. Other approximation methods may also be used.

Once the 3D coordinates of the object of interest are ascertained, where the 3D coordinate system is calibrated based on the centers of both eye balls, the viewing distance from each eye can then be easily determined.

The process of determining line-of-sight is called gaze tracking, which is related to eye tracking. The two terms are sometimes interchangeable, with the difference that eye tracking generally deals with determining the existence of eye(s) in the camera image, and also with tracking eye features such as the pupil and iris in order to determine the center of the pupil. Whereas gaze tracking generally deals with determining the line-of-sight, either in a 2D or 3D coordinate system, although gaze tracking often uses eye tracking results to help determine line-of-sight. Furthermore, because the fovea region (where the most visual attention resides) is slightly different from the intersection point of the optical axis and the retina, there is even a difference between line-of-sight and line-of-gaze, where the former is tied to the center of the fovea or the visual axis, and the latter is tied to the optical axis. In practice, we can only directly measure line-of-gaze, and the angular difference between the optical and the visual axis, if known, can then be used to derive the line-of-sight in a simple geometric manner. This value may be either measured for each patient, or for simpler implementation based on a population average. Further details of gaze tracking can be found, for example, in the publication *In the Eye of the Beholder: A Survey of Models for Eyes and Gaze*, Dan Witzner Hansen and Qiang Ji, IEEE Transactions on Pattern Analysis and Machine Intelligence. Vol. 32, No. 3. pp. 478-500. March 2010, the disclosure of which is incorporated herein by reference.

Eye and gaze tracking have been an important research topic for decades, and the field of eye and gaze tracking is still non-trivial, because of the greatly varying conditions of background lighting, difference(s) among eyes, head movement, and reflections from eyeglasses as interference, just to name a few variables or barriers.

Interestingly, many of these barriers can be avoided or greatly reduced when a gaze tracker is embedded into a pair of eyeglasses. For example, reflections from eyeglasses are no longer an issue because the gaze tracker can be placed on the inside of the eyeglasses. Controlled lighting, usually in the form of near infrared LED illumination, is generally used for indoor eye/gaze tracking but not effectively for outdoor eye/gaze tracking because background light interference from an outdoor environment is simply too strong. When embedded in eyeglasses, the LED(s) can be placed much closer to the eyes, facilitating higher SNR (signal-to-noise ratio) with respect to background lighting and/or lower power consumption (same illumination effect for less power at a closer distance). This advantage is exploited in many head-mounted eye/gaze trackers. In addition, instead of using a general IR passing filter that passes most IR light during image capture, a near-infrared narrow band filter may be used to block out most of the background light interference, and if that narrow band is designed to match the same narrow band light that a near infrared LED produces, it can amplify the LED signal to a larger signal-to-noise ratio on the order of 50:1 (compared to no IR filter) or about 8:1 (compared to general IR filter) for realistic implementations. More details will be given on this technique in the section describing the modified Smart CMOS image sensor proposed in the present disclosure. Note that near infrared light is usually used because it is invisible to the eye and does not cause the pupil to contract under its illumination, and that it can be captured on most CCD (Charge Coupled Device) and CMOS image sensors, because most of them use silicon based photo-sensors, which are relatively cheap to manufacture and may be sensitive to infrared light with wavelength up to about 1100 nm, although sensitivity drops quickly to zero beyond 1000 nm. Other infrared wavelengths may be used for eye/gaze tracking as well, provided image sensor technology is available to capture such wavelengths effectively.

Glint-Only Based Gaze Tracking

To support gaze tracking in eyeglasses, the gaze tracker must be easy to implement and be of low computational complexity and of low power, in order to facilitate a small size implementation. Therefore, eye glints may be used for gaze tracking. The eye under active illumination (which may be infrared or a visible light) of a point light source will generate several reflections, with the first reflection appearing on the outer surface of the cornea, and the corresponding generated point image being called the first Purkinje image, which is often referred to as the glint. Other reflections generate second, third and fourth Purkinje images, but the first Purkinje image is the brightest and thus the most suitable image for eye/gaze tracking purposes for low cost, low complexity implementations.

While most gaze tracking algorithms seem to focus on combining eye glints and pupil tracking to estimate the gaze, the method provided by the present disclosure utilizes eye glints. Because a glint is a point image, it may be easier to detect in image sensors, because it generally corresponds to one image sensor pixel or a small cluster of pixels. In later sections, the present disclosure will describe how to detect pixels corresponding to the glint with low power design. Low power consumption is important because the cameras that track the eyes and gaze must be part of the eyeglasses, and there may be very little room to integrate extra batteries and/or power supplies into the eyeglasses if a design goal is to keep the eyeglasses as compact as possible. Minimizing heat dissipation in the eyeglasses is also a goal, as patients must place the eyeglasses on their heads and comfort as well as safety are key considerations.

When the eyes rotate to see different objects, each eye rotates around the center of the eyeball, and the glint is a virtual image formed by the cornea, and the cornea is generally modeled as a spherical surface. If we use the center of the eyeball as the origin in a 3D coordinate system (with each eye having its own 3D system, but they can be easily converted to the other by measuring nominal inter-pupillary distance ahead of time), and if we know the 3D location of the LED as $(x_L, y_L, z_L)$, the curvature (i.e., radius) of the cornea as $r_c$, and the distance from origin to the spherical center of the cornea as $d_c$, then given the rotational angles of the eye in azimuth (horizontal angle) $\alpha$ and altitude (elevation angle) $\beta$, we can predict the 3D coordinate of the glint. The steps are as follows: first, we derive the cornea center's 3D coordinate $(x_c, y_c, z_c)$ based on polar geometry as $x_c = d_c \cos(\alpha)\cos(\beta)$, $y_c = d_c \sin(\alpha)\cos(\beta)$, $z_c = d_c \sin(\beta)$; next, we form a straight 3D line between LED $(x_L, y_L, z_L)$ and cornea center $(x_c, y_c, z_c)$; if we denote $d_L = \eta r_c$ as the distance between LED and cornea's spherical surface in the ratio of $r_c$, and denote $d_g$ as the distance between the virtual glint image and the cornea spherical surface along the 3D line, then according to optics equations for spherical mirrors, the virtual glint image must satisfy the equation $d_g = \eta r_c/(2\eta+1)$. Since $d_L$ can be easily computed as the Euclidean distance between $(x_c, y_c, z_c)$ and $(x_L, y_L, z_L)$ (denoted as $d_{cL}$) minus $r_c$, $d_g$ can be easily derived as well, and since the glint must fall on the 3D line, given $d_g$ its 3D coordinate can also be derived with simple 3D geometry.

Figure 3:
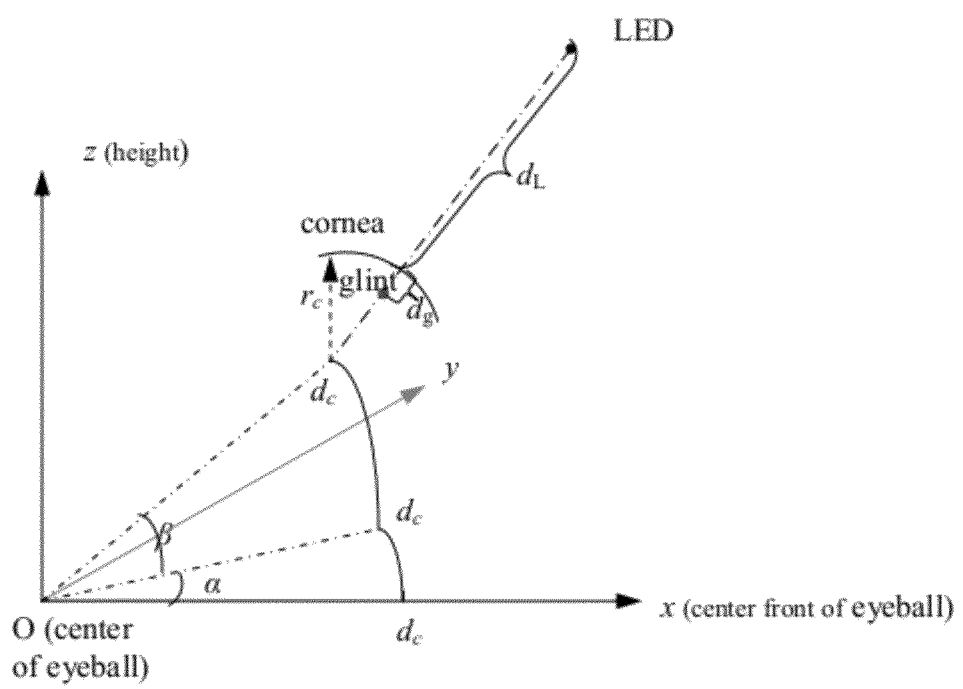
FIG. 3 shows an illustration of a rotational angle pair (azimuth α and altitude β) in eye or gaze tracking according to an embodiment of the present disclosure.

FIG. 3 shows an illustration of a rotational angle pair (azimuth α and altitude β) in eye or gaze tracking according to an embodiment of the present disclosure. Graph 300 illustrates the 3D relationship among eyeball center (Origin), cornea center without and with rotation, LED, and the glint. Note that the distance between Origin and cornea center $d_c$ is always constant for the same user, as long as there is no significant physical change to the eye. The dot underneath the text "glint" may be the virtual glint image. The optical equations discussed above also apply to graph 300.

Conversely, if we know all other parameters, including the 3D coordinates of the glint, and want to compute the two rotational angles, we can achieve that by plotting a 3D line from the LED to the glint, and the spherical center of the cornea must then reside on that line (thus having 1 degree of freedom). Let that center's 3D coordinate be denoted $(x_c, y_c, z_c)$, then at the same time, it must reside on a spherical surface with center at origin and radius of $d_c$, with the equation $x_c^2 + y_c^2 + z_c^2 = d_c^2$. Let t denote the distance from the LED toward the eye along that 3D line, because $(x_c, y_c, z_c)$ also falls on that line, we can infer that all points on the line, including $(x_c, y_c, z_c)$, can be expressed with the parameter t in one-degree linear form. Therefore, the equation $x_c^2 + y_c^2 + z_c^2 = d_c^2$ becomes a quadratic equation of t, which can be solved easily. Note that only 1 out of 2 roots of the quadratic equation is valid, since the line specified by t can only intersect with a spherical surface toward the front of the eye instead of the back of the eye. Using the valid root of t, we can then obtain $x_c, y_c, z_c$. Then, we can obtain the rotational angle pair (azimuth α and altitude β) easily according to the definition of polar geometry.

The 3D coordinate of the glint can also be obtained if we use 2 cameras whose 3D coordinates and focal lengths are known, in a similar manner to stereoscopic vision.

The above method assumes many eye-specific parameters are known, which requires calibration. A calibration-free gaze-tracking method is described in *A Calibration-Free Gaze Tracking Technique*, Sheng-Wen Shih et al., International Conference on Pattern Recognition. pp. 201-204. 2000, the disclosure of which is incorporated herein by reference. This method can be used to derive some of these parameters using 2 LEDs and 2 cameras, assuming the relative 3D coordinates of the point(s) between the LEDs and cameras are known (and this is relatively easy to satisfy, since they are most likely to be mounted steadily on the eyeglasses, thus allowing simple pre-calibration during manufacturing). The calibration-free method can recover the 3D coordinate of the cornea center relative to the cameras, and with that the 3D coordinate of the glint can also be determined. Although this method does not recover $d_c$ and $r_c$ directly, if the user is asked to rotate his/her eyes to a variety of angle pairs, it is evident that the trace of cornea center 3D coordinates will follow a spherical surface with a radius of $d_c$ and with its center at the center of the eye. Therefore, by collecting enough samples of 3D coordinates of the cornea center, a regression on a spherical surface can be performed and hence $d_c$ and the 3D coordinate of the center of the eye can be recovered relative to the cameras, and then all 3D coordinates can also be easily converted to using the center of the eye as the origin, as is the case in previous paragraphs and FIG. 3. To recover $r_c$, it is sufficient to realize that $d_L = \eta r_c = \sqrt{(x_c - x_L)^2 + (y_c - y_L)^2 + (z_c - z_L)^2} - r_c = d_{cL} - r_c$, where $(x_L, y_L, z_L)$ is the 3D coordinate of the LED and is known, which implies $d_{cL}$ is also known. So η can be expressed as $d_{cL}/r_c - 1$ (a function of $r_c$), and $d_g = \eta r_c/(2\eta+1) = r_c - d_{cg}$ where $d_{cg}$ is the distance between cornea center and glint and is also known. We can then plug in the expression of η in terms of $r_c$, and solve the equation $d_g = \eta r_c/(2\eta+1) = r_c - d_{cg}$ on the unknown variable $r_c$. More precisely, the equation to solve simplifies to $(d_{cL} + d_{cg})^* r_c - 2 d_{cL}^* d_{cg} = 0$, or simply as $r_c = 2 d_{cL}^* d_{cg}/(d_{cL} + d_{cg})$. Multiple measurements may be made to estimate $r_c$, for example, by averaging, to make the estimation of $r_c$ more accurate. Because $d_c$ and $r_c$ are user-specific parameters and don't change, they only need to be determined once per user. So, combined with the procedure just described, the calibration-free method can also recover the relative 3D positions between the LEDs and the eyeball center. Therefore, one can use the algorithm described by Sheng-Wen Shih et al. in *A Calibration-Free Gaze Tracking Technique* combined with the procedure just described to auto-calibrate the eyeglasses at time of initial use, and later that algorithm alone can be used to re-estimate 3D coordinate of the cornea center relative to the cameras and thus to compensate for eyeglass slippage, but at a lower frequency than tracking frequency to save LED power and computing power during recalibration. Then once slippage is compensated, only 1 LED and 2 cameras are needed to generate the 3D coordinates of the glint. In addition, the tracker may switch to a different LED (but still use 1 LED at a time) if the other LED is expected to provide a more clear glint. This may happen because sometimes the eye is rotated so much that the glint does not actually form from a particular illumination direction, thus having 2 LEDs and switching intelligently between them will likely provide better results. Although the algorithm described by Sheng-Wen Shih et al. in *A Calibration-Free Gaze Tracking Technique* already implements gaze-tracking and is calibration-free, it requires analysis of the eye pupil image in order to perform gaze-tracking, and such analysis may be too complex for an embedded circuitry on the eyeglasses to handle. Therefore, by utilizing the algorithm described by Sheng-Wen Shih et al. along with the procedure above to auto-calibrate the eye parameters, and then use just the algorithm described by Sheng-Wen Shih et al. to compensate for slippage, gaze tracking becomes much simpler with the steps described above in this disclosure. Alternatively, the eye parameters, specifically, $d_c$ and $r_c$, may be measured for a user at the time of determining myopia prescription. Note that the 2 LEDs are for each eye. For both eyes, up to 4 LEDs may be needed, although it may be possible to share 1 LED and even 1 camera by placing the shared LED and camera near the center between two eyes, thus potentially reducing the total to 3 LEDs and 3 cameras per user.

Figure 12:
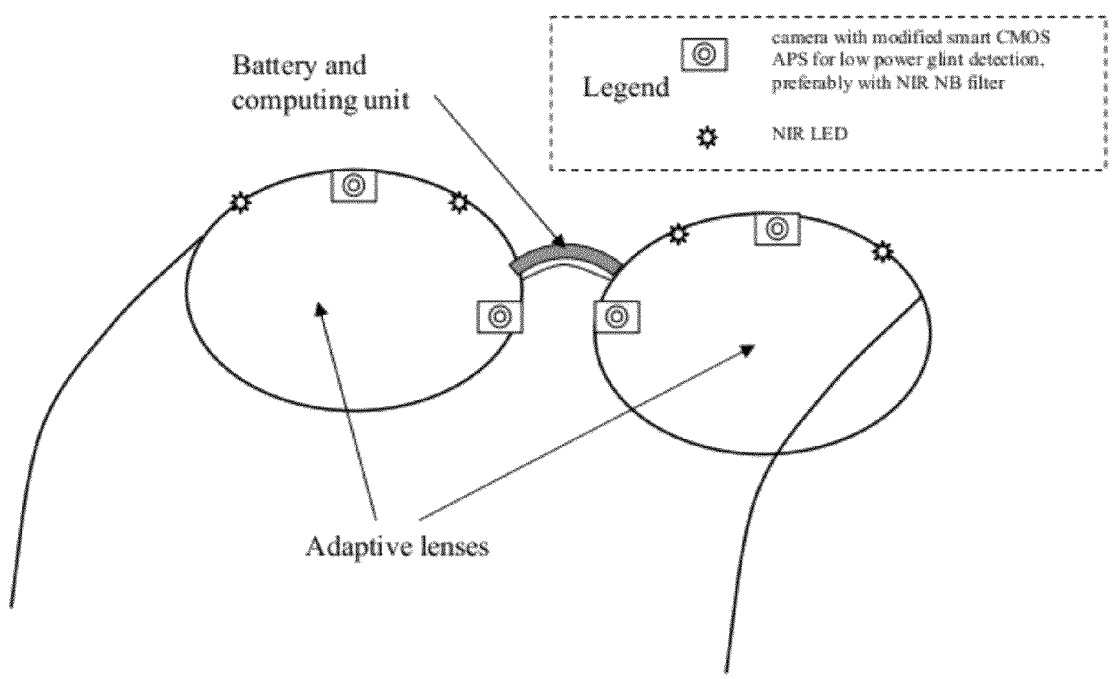
FIG. 12 shows an example of a pair of eyeglasses with adaptive lenses and gaze tracking, according to an embodiment of the present disclosure.

FIG. 12 illustrates a pair of eyeglasses with adaptive lenses and gaze tracking, with 2 LEDs and 2 cameras per eye. The battery, as well as computing unit that computes gaze distance from glint information, may be placed in an aesthetically acceptable position, e.g., in the middle of the eyeglasses, as in FIG. 12. The LEDs, cameras, battery and computing unit may be connected by physical wires that follow the same contour as that of the eyeglasses. Alternatively, the battery and/or computing unit may be placed along edges of the eyeglass frame, or on the sidebar(s) of the eyeglasses. The positions of LEDs and cameras are illustrative only, and other positions yielding better gaze tracking performance may exist. The cameras in FIG. 12 should use modified smart CMOS APS for low power glint detection, which will be described in detail in later sections.

The 1 LED, 2 camera configuration is actually a slightly over-determined system. Once the gaze tracker in the eyeglasses is calibrated automatically with the algorithm in the Appendix or pre-calibrated, for each unique pair of rotational angles, there is a unique 3D coordinate for the glint, which would map to a unique 2D coordinate on the camera's image sensor plane. So there exists a one-to-one mapping between a rotational angle pair and a 2D camera glint coordinate, and consequently, given a 2D camera glint coordinate, we can map it back to a 3D coordinate and also a rotational angle pair, thus obtaining gaze tracking information. This would only require 1 LED and 1 camera after auto-calibration or pre-calibration. Unfortunately, the reverse mapping (from 2D to 3D or rotational angle pairs) may be highly complex and does not appear to have closed form equations, therefore one may have to solve it approximately by some form of iterative interpolation such as, for example, Newton approximation, or pre-compute a complete forward mapping from rotational angles to 2D glint coordinates with a high enough sampling density so that every pixel in the camera image sensor array that may have a glint has at least one rotational angle pair corresponding to it. Then, a reverse mapping can be constructed by computing the average rotational angle pair within each such pixel.

Approximate solutions may increase the computational complexity for each tracking, while pre-computation may be computationally intensive and should not be done for every re-calibration. If the goal is to save hardware cost, then pre-calibration, pre-computation of reverse mapping and 1 LED with 1 camera may be used, but this configuration cannot compensate for the slippage of the eyeglasses. If auto-calibration is used, then 2 LEDs and 2 cameras may be needed anyway, and it would seem less useful to use 1 camera and have to redo pre-computation of reverse mapping during slippage when 2 cameras would give a low complexity solution and also provide easy re-calibration for slippage purposes.

Therefore, the preferred embodiment for the gaze tracker is to use 2 LEDs and 2 cameras for auto-calibration during initial use, and then switch to 1 LED and 2 cameras for glint-based gaze tracking, where the active LED may be changed based on which LED is most likely to generate a more visible glint image, and where re-calibration may be performed at a frequency less than tracking frequency to compensate for slippage. Alternatively, if slippage is expected to be small, a secondary embodiment comprises 1 LED and 1 camera with pre-calibration and pre-computation of a reverse mapping between a 2D glint coordinate and a rotational angle pair.

Once the rotational angle pairs are derived for each eye, both lines-of-gaze are available. Then, the angle between the visual and the optical axis, either pre-calibrated, or based on a population average, can be used to convert lines-of-gaze to lines-of-sight. Then, the intersecting point of lines-of-sight represent the 3D coordinates of the object of interest, and its viewing distance can then be easily derived for each eye, which can then be used to drive the optical power of the adaptive lens(es) according to one of three aforementioned accommodation reduction modes.

When the eye blinks, if the eye lid has not completely closed and the glint is still visible to the camera (or visible to both cameras in the preferred embodiment), the methods above can still detect the glint and obtain gaze tracking information. If the eye lid closes sufficiently, the glint will be invisible, and the gaze tracker will not be able to obtain tracking information. However, if the eye is either closed or sufficiently closed, which means the eye is not seeing anything useful, the gaze information is essentially irrelevant. The gaze tracker may use the last known gaze tracking information in such cases, and in fact, whenever the gaze tracker fails to obtain tracking information for some reason (such as no glint detected), it may use the last known corresponding information instead. The glint detection circuit, which will be described later in this disclosure document, can notify the gaze tracker that no glint is detected during an image capture.

Low-Power Glint Tracking for Smart CMOS Image Sensors

A gaze tracker suitable for use in eyeglasses must be not only easy to implement and of low computational complexity, but also consume low power, because there is very little space for batteries in an eyeglass frame. Considering that the adaptive lens(es) may already consume a noticeable share of the battery capacity, it is highly preferred that the gaze tracker consume very low power, e.g., in the sub-mW range.

There are mainly 4 components of power consumption in a gaze tracker: (i) LED lighting, (ii) image capture, (iii) eye feature detection, and (iv) gaze computation. Gaze computation in the aforementioned preferred embodiment with 2 LEDs and 2 cameras involves very little computation, and mainly requires the obtaining of the 3D coordinates of the glint from 2 cameras, solving a quadratic equation and subsequently deriving the rotational angle pair, the lines-of-sight and the lines-of-gaze, and the gaze distance for each eye. It is likely to cost less than 100 floating point computation cycles per tracking. Therefore, gaze computation is expected to consume very little power. The first three factors are thus more important and the subject of the following description.

Near infrared LEDs typically consume a few to tens of mW, and radiate (e.g., in near infrared photons) a fraction of their consumed power. This fraction may be, for example ⅓, and this amount will be used as an example to illustrate power consumption. For an example of the use of this fraction, see the datasheet *MOLD LED Lamp L*880 *Series: Infrared LED Lamp. Marubeni America Corporation*, which is incorporated herein by reference. With the preferred 2 LEDs, 2 cameras configuration, we may use 1 LED and 2 cameras after auto-calibration, and this will result in savings of roughly one half of the LED power.

Both CCD and CMOS image sensors are sensitive to near infrared light. However, since CMOS sensors generally have lower power consumption, and also support random access, CMOS sensors are the preferred choice of image sensors for the present disclosure. Also, CMOS facilitates the combination of image capture and intelligent signal processing because the photo-sensors and CMOS signal processing elements can be manufactured in the same physical process. This is called a Smart CMOS image sensor, and it is a rapidly progressing field. The following sections describe a modified Active Pixel Sensor (APS) element in a Smart CMOS image sensor that may achieve glint detection at very low power.

Modified APS with a PMOSFET Source Follower

First, it is observed that in conventional eye/gaze tracking, the entire eye image is captured, usually as a grayscale or color image, and analyzed further. In our glint-only based gaze tracking method, we only need to detect the glint, which is generally much brighter than other eye features. This means that we can reduce the exposure time of image capture such that the glint will still appear strongly, whereas other features will appear mostly as dark or close to dark pixels. This reduction in exposure time can save LED power, because we don't have to spend extra exposure time to capture the eye features that we don't intend to use in our method.

Second, most of the power consumption in a CMOS image sensor circuit is due to active current flowing through a monitoring transistor, where the current is partly controlled by the voltage of the photo-sensor (typically a photodiode), and that voltage changes depending on the amount of incident light.

Figure 4:
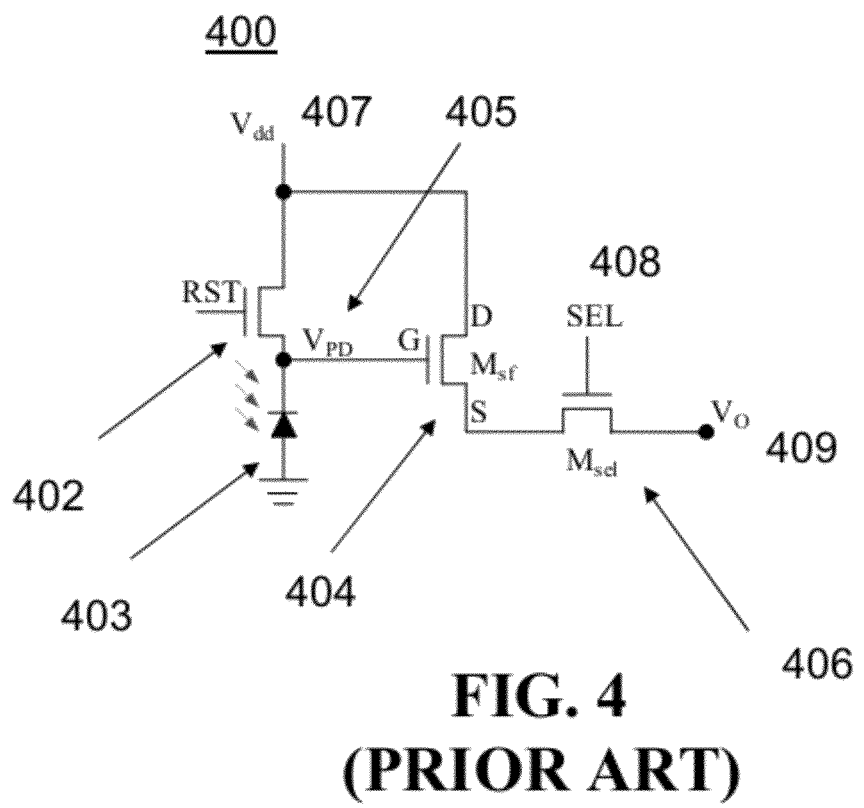
FIG. 4 shows a conventional 3-transistor Active Pixel Sensor (3T-APS).

FIG. 4 shows a conventional 3-transistor Active Pixel Sensor (3T-APS). APS 400 is known in the prior art and includes reset transistor 402, photodiode 403, source-follower transistor 404, photodiode voltage 405, select transistor 406, supply voltage 407, select signal 408, and output voltage 409. The basic building block unit in a CMOS image sensor is an Active Pixel Sensor (APS), where the photo-sensor is reverse-biased (as illustrated by photodiode 403 which takes in light shown by the series of three arrows) and usually charged to an initial positive voltage (e.g., Vdd as reflected by supply voltage 407), and then light exposure reduces that voltage, and the reduced voltage then is used to control the Gate of source-follower transistor 404 and consequently the current flowing through the source-follower transistor 404. The photodiode voltage 405 ($V_{PD}$) is initialized to the difference of Vdd−Vth during reset. Here Vth is the threshold voltage of a transistor (e.g., MOSFET), and in this case, the reset transistor 402.

Recall from analog electronics that in an nMOSFET (the more commonly used type), current flows from Drain to Source only if Gate to Source voltage $V_{GS}$ exceeds its Vth, or threshold voltage. Conversely, in a pMOSFET, the same path conducts (but flows from Source to Drain) only if $V_{GS}$ is smaller than its Vth (which is negative). For simplicity, we may assume Vth is about the same across all MOSFETs in the same CMOS image sensor (for pMOSFETs, Vth will be negative but we can assume its absolute value is about the same), since they might be manufactured in the same manner. However, one may also combine MOSFETs with different Vth values to achieve some novel design functionality. In FIG. 4, Msel or select transistor 406 may be a MOSFET that conducts when its corresponding APS is selected for reading through the select signal 408 (shown as SEL in FIG. 4). The use of reverse-bias and subsequent voltage reduction is referred to as the accumulation mode, and is the most common mode for photodiodes, as described, for example, at pages 29-35 of *Smart CMOS Image Sensors and Applications*, Jun Ohta, ISBN 0-8493-3681-3 CRC Press. 2008, which is incorporated herein by reference.

Because the voltage of the photo-sensor $V_{PD}$ or photodiode voltage 405 decreases instead of increasing during light exposure, it means that Msf or the source-follower transistor 404 will turn on and consume current when a pixel is dark, but as the pixel turns white, the current will reduce and eventually the current may stop flowing. This means that a darker image will generally consume more current than a whiter image for such a design of APS (shown in FIG. 4), which is commonly used in the prior art. For glint detection, however, we are only interested in glint pixels, e.g., white pixels, and there should be very few of them in one captured image. If we reduce the exposure time of LED lighting to save LED power, the conventional APS design shown in FIG. 4 will actually consume more power because most pixels will be black, and that is not desirable. Therefore, an APS that consumes less power when most pixels are black is highly desirable.

Figure 5:
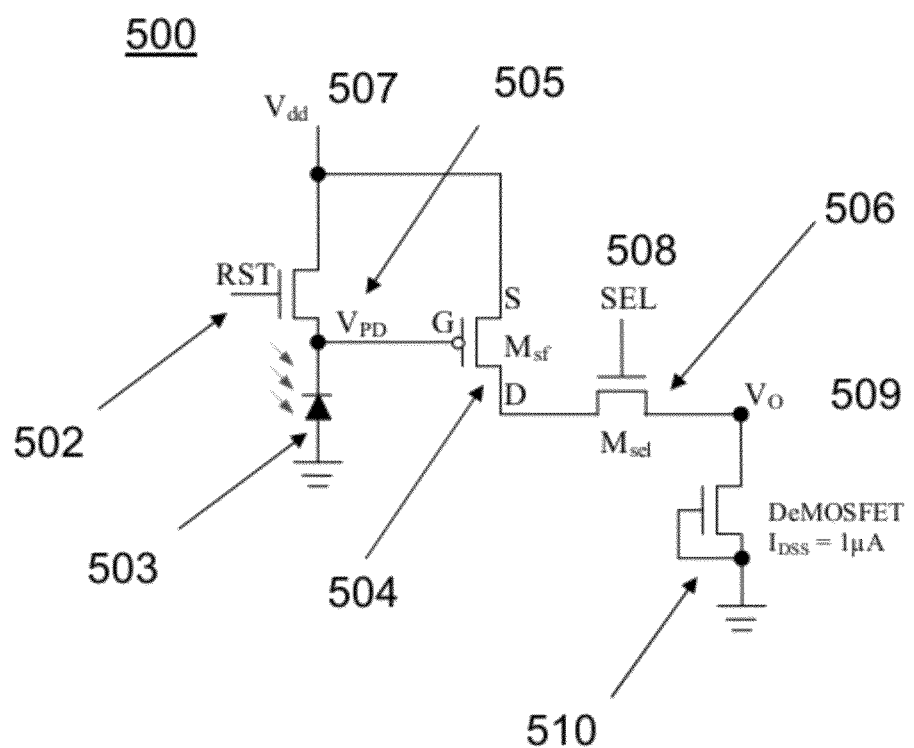
FIG. 5 shows a modified 3T-APS with a current limiter, according to an embodiment of the present disclosure.

FIG. 5 shows a modified 3T-APS with a current limiter, according to an embodiment of the present disclosure. APS 500 includes reset transistor 502, photodiode 503, source-follower transistor 504, photodiode voltage 505, select transistor 506, supply voltage 507, select signal 508, output voltage 509 and current limiting transistor 510. APS 500 is a low-power glint-only detection design that consumes less power when most pixels are black and more suited for glint detection. Components 502-509 are similar to components 402-409 of FIG. 4 with some slight modifications. In one embodiment, the source-follower transistor 404 (which may be an nMOSFET) may be changed to a pMOSFET, for source-follower transistor 504, thereby reversing the positions of Drain and Source pins for the source-follower transistor 504. Now, when a pixel is not a glint, it will be black or close to black, and the photo-sensor's voltage will be high, close to Vdd; since for a pMOSFET its Source is connected to Vdd (supply voltage 507), as long as the Gate voltage (i.e., photo-sensor voltage) is high and close to Vdd, the pMOSFET will remain turned off.

We can calibrate the gaze tracker (e.g., exposure time) such that under most conditions, a glint caused by LED illumination will cause the photo-sensor to change the voltage by more than Vth, the threshold voltage of the pMOSFET, whereas non-glint pixels will not be able to decrease their voltage by Vth or more. Consequently, all non-glint pixels will have their pMOSFETs turned off and consume essentially no current. Glint pixels will have their pMOSFETs turned on and consume some current, but the total number of such pixels will be very small. If we add a current limiter to the pMOSFET, such as, for example, a large resistor or current limiting transistor 510, we can further control the amount of power consumed. In one embodiment, the current limiter may be in the form of a large resistor of say several Mega Ohms. In one embodiment, the current limiter may be in the form of current limiting transistor 510, which may be more convenient for large scale integration. In one embodiment, current limiting transistor 510 may be a DeMOSFET (Depletion Enhancement MOSFET) with a small 0V Drain-to-Source saturation current ($I_{DSS}$) of say 1 μA. When reading 1 scan (horizontal) line (row), if we expect ≤10 glint pixels, and Vdd=3V, $I_{DSS}$=1 μA, then the peak power from all APS in that line may be ≤3*10*1 μW=30 μW.

Figure 6:
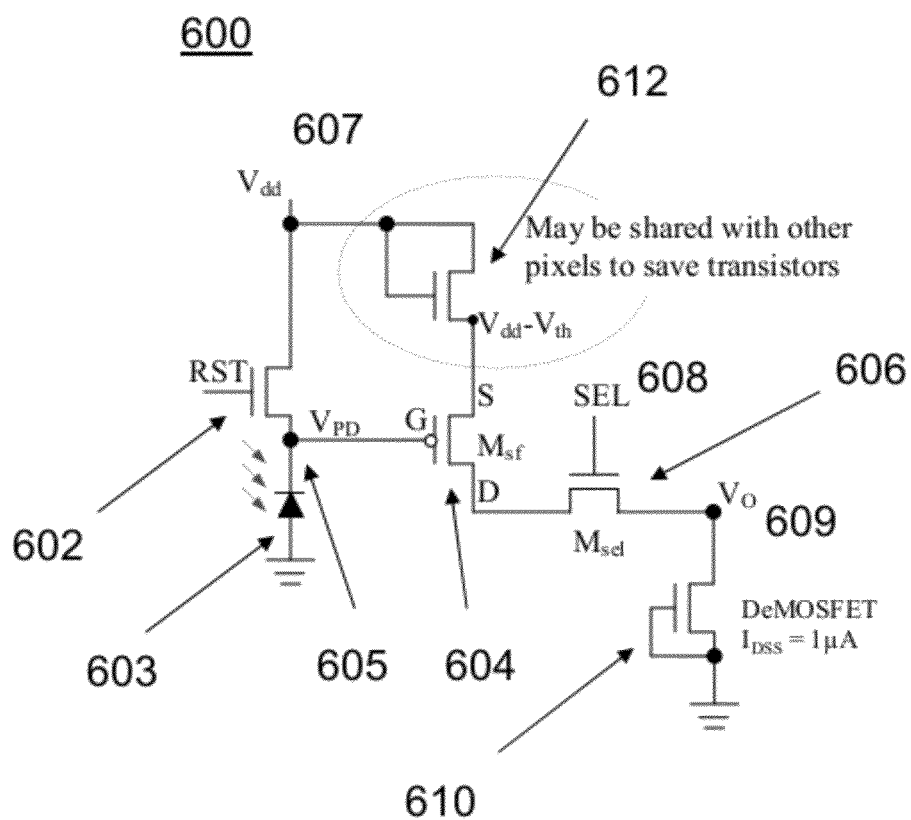
FIG. 6 shows a modified 3T-APS with a shared transistor, according to an embodiment of the present disclosure.

In actual implementation, because an nMOSFET (e.g., reset transistor 502) is generally used to reset the photodiode 503 to full reverse bias, and the reset signal at its Gate typically uses the same power supply voltage 507, e.g., Vdd, and this nMOSFET's Source pin is connected to the photodiode 503, and because MOSFETs requires Gate-to-Source voltage ($V_{GS}$) to be higher than Vth to turn on the MOSFET, the photodiode 503 may be able to charge to Vdd−Vth in a design as shown in FIG. 5. This is a well-known issue or behavior in CMOS APS design. Therefore, in our modified APS, the $V_{GS}$ of Msf or source-follower transistor 504 will start at (Vdd−Vth)−Vdd=−Vth, instead of 0. That means Msf or source-follower transistor 504 will turn on as soon as a little bit of light is present, instead of needing much more light. To solve this problem, either a pMOSFET can be used in 502 to ensure a reset to full Vdd, or we can use an additional nMOSFET to drop the Source voltage of Msf or the source-follower transistor 504, as shown in FIG. 6. This additional transistor can be shared among all pixels, therefore has negligible overhead.

FIG. 6 shows a modified 3T-APS with a shared transistor, according to an embodiment of the present disclosure. APS 600 includes reset transistor 602, photodiode 603, source-follower transistor 604, photodiode voltage 605, select transistor 606, supply voltage 607, select signal 608, output voltage 609, current limiting transistor 610, and shared transistor 612. Components 602-610 of APS 600 are similar to components 502-510 of APS 500. Shared transistor 612 drops the source voltage of source-follower transistor 604 to Vdd−Vth, which matches the initial photodiode voltage $V_{PD}$ 605 after a reset, as a solution to the problematic case of when source-follower transistor 604 turns on as soon as a little bit of light is present (when much more light should have been needed). Shared transistor 612 may also be shared amongst multiple pixels to save transistors and transistor space, and therefore has negligible overhead.

CMOS image sensor arrays facilitate random access, and they also may enable an entire row of pixels to be sensed, much like other 2D layout circuits. Therefore, we may place the aforementioned resistor or DeMOSFET (of current limiter, represented as current limiting transistor 510, 610 in FIGS. 5 and 6) at each column, and access all APS elements in a row simultaneously. After enumerating all rows in the sensor array, the entire captured image will have been processed. The output voltage of the pMOSFET is suitable for CMOS logic input. Therefore, conventional logic design may be used to perform any logic processing that is desired. For example, the MOSFET output may be sent to a row of latches or registers to store their values. Then, the pMOSFET can be disengaged with another control transistor (e.g., Msel 508, 608, which is used anyway) to reduce power consumption. Then, we can use a priority encoder circuit (discussed, for example, in Priority Encoders, www.electronics-tutorials.ws/combination/comb_4.html, which is incorporated herein by reference) to select one of the glint pixels (which would have a different voltage and logic value than non-glint pixels), and output its column number. That pixel can then be cleared from the priority encoder circuit and the next glint pixel on the same row can be selected and its column number displayed, until all glint pixels in that row are displayed. This above-described process is based on CMOS logic and is expected to consume very low power as well.

It is possible a glint may correspond to a small cluster of pixels instead of just one pixel in the CMOS image sensor array. This can be detected by grouping glint pixels by their 2D coordinates and relative proximity in the sensor array, which may preferably be done in software since the number of such pixels is expected to be small.

Alternatively, a Winner-Take-All (WTA) circuit (discussed, for example, in *A 200 μs Processing Time Smart Image Sensor for an Eye Tracker Using Pixel-Level Analog Image Processing*, Dongsoo Kim and Gunhee Han, IEEE Journal of Solid-State Circuits. Vol. 44, No. 9, pp. 2581-2590. September 2009, which is incorporated herein by reference) instead of a priority encoder circuit may be used to sense either the output voltage or current of the pMOSFET, and output the winner (which has the highest voltage or current and which corresponds to brightest pixel), and then select the next winner, and so forth. This approach has the advantage of selecting glint pixels strictly based on their brightness (as opposed to some arbitrary tie-breaking logic in priority encoders), one at a time. However, WTA circuits are generally slower than CMOS logic circuits, which may be an issue for a variant of the glint-detection method which we will describe later.

Figure 7:
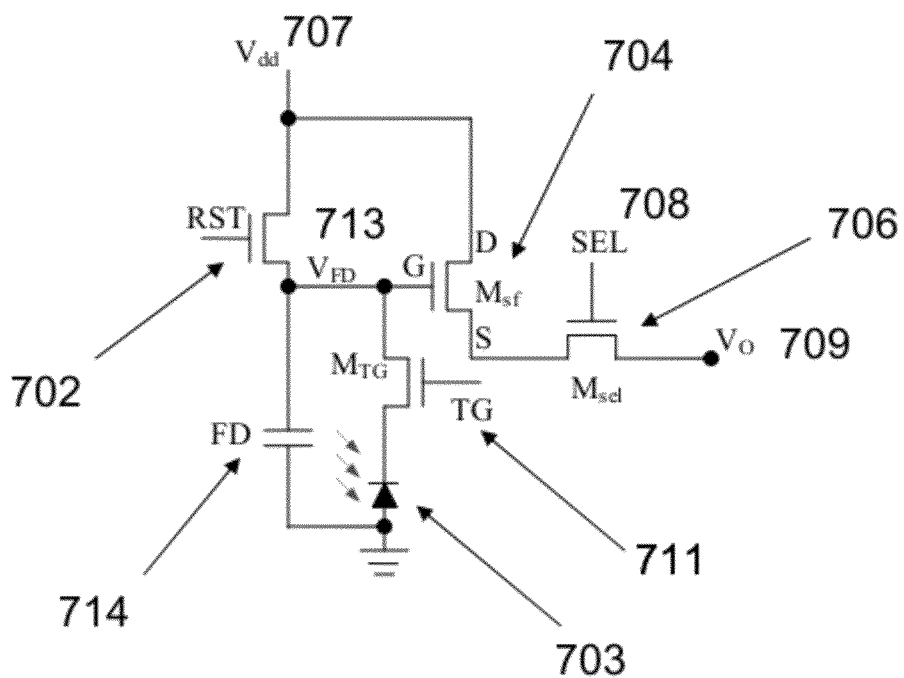
FIG. 7 shows a conventional 4-transistor APS (4T-APS).
Figure 8:
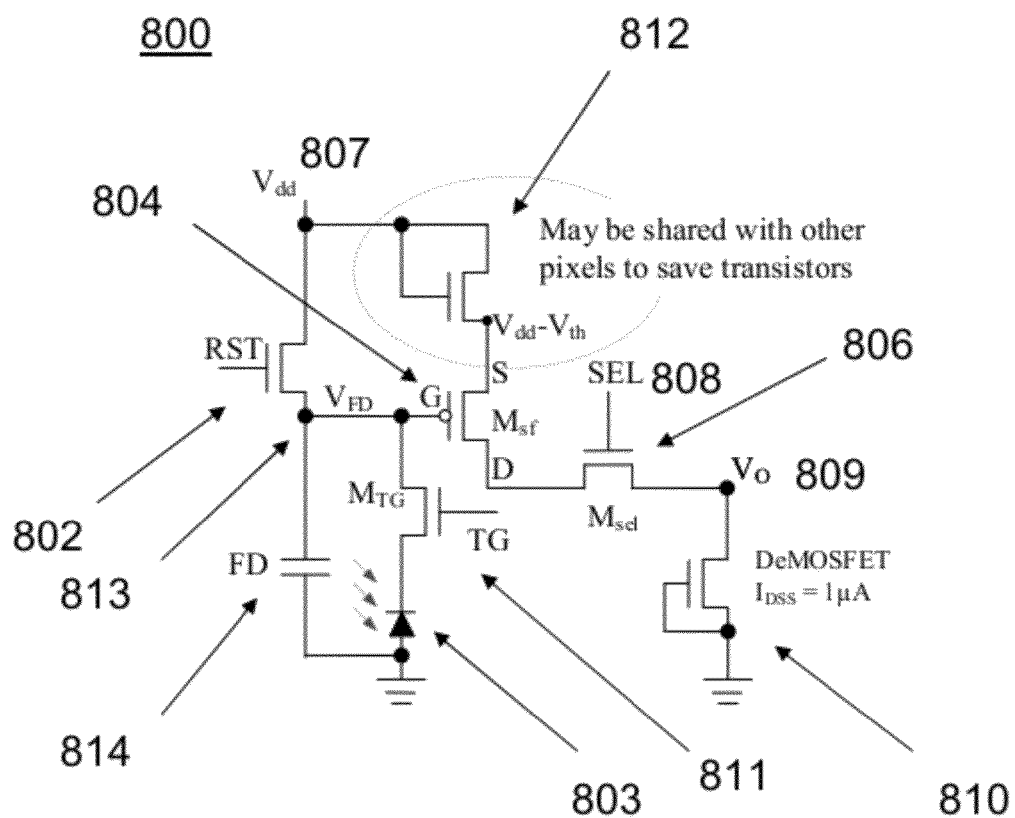
FIG. 8 shows a modified 4T-APS with a current limiter and a shared transistor, according to an embodiment of the present disclosure.

The pMOSFET based Msf or source-follower transistor 604 (and also 504) can also be used for other types of APS, such as a 4T-APS (4-Transistor Active Pixel Sensor) (e.g., 804 in FIG. 8) as long as the photo-sensor is reset in reverse-bias mode and uses accumulation mode. A conventional 4T-APS and its adaptation for low power glint detection are illustrated in FIGS. 7 and 8, respectively. Note that the charge from the photodiode in FIGS. 7 and 8 is transferred to a Floating Diffusion (FD) capacitor upon a high signal of TG, a design used to reduce sampling noise in CMOS image sensors (for more detail, see p. 39-42 of *Smart CMOS Image Sensors and Applications*, Jun Ohta, ISBN 0-8493-3681-3, CRC Press, 2008, which is incorporated herein by reference).

FIG. 7 shows a conventional 4-transistor APS (4T-APS). APS 700 is known in the prior art and includes reset transistor 702, photodiode 703, source-follower transistor 704, select transistor 706, supply voltage 707, select signal 708, output voltage 709, transfer gate transistor 711, floating diffusion voltage 713, and floating diffusion capacitor 714. Elements 702-704, 706-709 are similar to the corresponding reference characters in FIGS. 4-6, so a redundant description is omitted. If the TG signal feeding into transfer gate transistor 711 goes high, then the charge from photodiode 703 is transferred to the floating diffusion capacitor 714. This approach is designed to reduce the sampling noise in a CMOS image sensor.

FIG. 8 shows a modified 4T-APS with a current limiter and a shared transistor, according to an embodiment of the present disclosure. APS 800 includes reset transistor 802, photodiode 803, source-follower transistor 804, select transistor 806, supply voltage 807, select signal 808, output voltage 809, current limiting transistor 810, transfer gate transistor 811, shared transistor 812, floating diffusion voltage 813 and floating diffusion capacitor 814. Components 802-804, 806-814 are similar to the components in the previous Figures, however it is to be noted that source-follower transistor 804 may be a pMOSFET, and that shared transistor 812 may be shared amongst multiple pixels to save transistor space, similar to shared transistor 612 in FIG. 6. Furthermore, similar to FIG. 7, if the TG signal feeding into transfer gate transistor 811 goes high, then the charge from photodiode 803 is transferred to the floating diffusion capacitor 814. Again, this approach may help reduce the sampling noise in APS 800.

It is noted that the pMOSFET may require an N-substrate, which is opposite to the P-substrate used in most photodiode based photo-sensor designs. This may increase the manufacturing complexity accordingly. However, changing the photodiode to an N-substrate (and reverse-biasing it with Ground and Vdd swapped because reverse-biasing is necessary for accumulation mode operation) cannot avoid this manufacturing complexity, because one will find that an nMOSFET source follower will now be needed to ensure the same power-saving behavior. Therefore, a MOSFET of the opposite substrate to that of the photo-sensor is needed to provide low power glint detection. An equivalent circuit for an N-substrate photodiode with an nMOSFET Msf may have Ground and Vdd swapped and also have the photodiode flipped. An abbreviated example of a 3T-APS with an N-substrate photodiode and an nMOSFET Msf is illustrated in FIG. 9.

Figure 9:
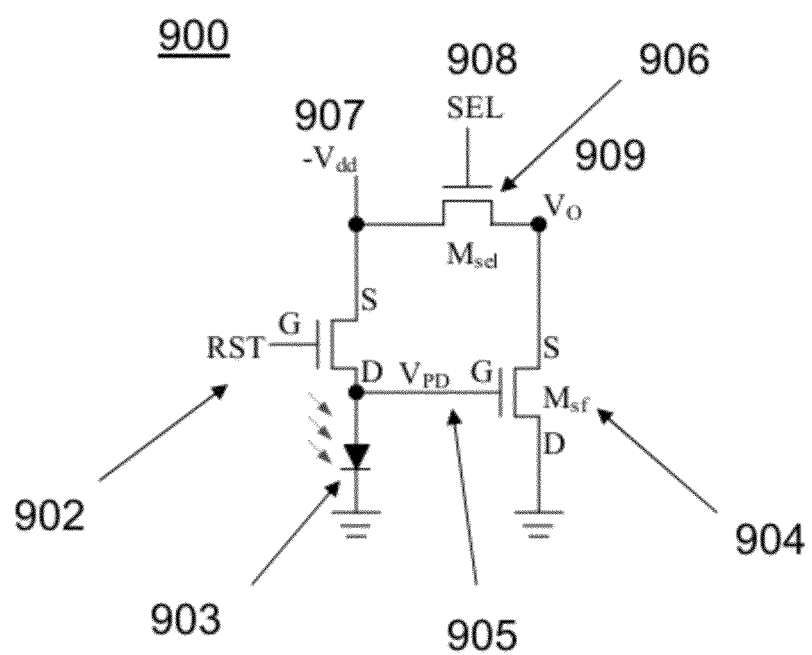
FIG. 9 shows a modified 3T-APS implementing low-power glint detection with an n-substrate photodiode, according to an embodiment of the present disclosure.

FIG. 9 shows a modified 3T-APS implementing low-power glint detection with an N-substrate photodiode, according to an embodiment of the present disclosure. APS 900 includes reset transistor 902, photodiode 903, source-follower transistor 904, photodiode voltage 905, select transistor 906, supply voltage 907, select signal 908 and output voltage 909. Components 902-909 are similar to similar reference characters in previous Figures, with the exception that an N-substrate photodiode is used for photodiode 903 that is oriented in a different direction than the photodiodes of the prior Figures. APS 900 may also have a reset signal of 0V during reset that feeds into reset transistor 902, and a value of −Vdd (negative) for the supply voltage 907. Note again that photodiode 903 is an N-substrate photodiode and flipped from the orientation of the photodiodes in the prior Figures. In addition, the Drain and Source pins of the reset transistor 902 and the source-follower transistor 904 are also flipped when compared with previous Figures. Using nMOSFET and an N-substrate photodiode may also achieve low power glint detection.

Effect of Near Infrared Narrow Band Filter in Blocking Background Light Interference This section of the present disclosure will also illustrate how much photocurrent is expected to be generated by a typical photodiode, and therefore, how much of a voltage drop is expected for a certain exposure time. A silicon based photodiode generally has about 0.1 A/W sensitivity at about 880 nm near infrared wavelength, which is the wavelength typically used for eye/gaze tracking. If we use 1 LED per eye with 2 mW consumed power, and ⅓ of it becomes infrared radiation, then the illumination power may be 0.667 mW per eye. Assume the cornea occupies about 10% of the illuminated area and assuming relatively uniform illumination, the cornea gets 10% of the 0.667 mW radiation. Now, we further assume each camera occupies about 1/1000 of the complete $2\pi$ hemisphere solid angle of the reflected illumination, and assuming the skin and the eye can reflect 50% of IR light (which is probably over-estimated), the camera lens now receives at most 0.5*0.667 mW*1/1000=333 nW of total reflected illumination. With a 100×100 pixel array, each pixel receives at most 333 nW/10000=33.3 pW. At 0.1 A/W, each photodiode will generate 0.1*33.3=3.33 pA of photo current. According to at least p. 29-31 of *Smart CMOS Image Sensors and Applications*, for example, such a current will typically take about 100 ms for the photodiode voltage to drop from Vdd of 3V to close to 0V, where the decrease is roughly linear with respect to the exposure time and photo current (see p. 29-31 of *Smart CMOS Image Sensors and Applications*, for example, for a more exact analysis).

Now, in comparison, for a glint pixel, assuming the entire glint fits in one pixel, and assuming the cornea has a 2.4% reflectivity (See, for example, *Video-based eyetracking methods and algorithms in head-mounted displays*, Hong Hua and Prasanna Krishnaswamy. 15 May 2006/Vol. 14, No. 10/OPTICS EXPRESS, which is incorporated herein by reference) to near infrared light, the glint pixel will receive 0.024*0.1*0.667 mW*1/1000=1.6 nW. Thus, the photodiode at the glint pixel will generate 0.1*1.6=160 pA of photo current. This gives an SNR of at least 160:3.33=48:1 between glint and non-glint pixels assuming no background light interference. This is because a significant amount of glint light is focused into a single pixel. Such amplification due to glint concentration can be estimated by recognizing that a 100× 100 pixel array has 10000 elements, therefore the amplification ratio due to such concentration is roughly 0.024*0.1*10000=24. Note that although we may use a 1000×1000 pixel array and achieve an even higher amplification ratio, this would increase cost, and because the LED is not necessarily a perfect point light source, and because the cornea's virtual glint image is not strictly a single point (even a perfect spherical mirror does not produce a single point image but rather an image with a small tail), the glint may spread to a small cluster of pixels, and may be less convenient to process than a single glint pixel. Note that using Ohta's (p. 29-31 of *Smart CMOS Image Sensors and Applications*) guidelines, 160 pA current will typically take about 100 ms/48=2 ms to drop from a Vdd of 3V to close to 0V. In practice, we don't need a drop as much as 3V, in fact, a slightly higher than Vth drop is good enough. If Vth=0.7V, then for example we can designate 1.25*Vth=0.875V as the desired drop, and it may take only about 0.875V/3V*2 ms=0.58 ms exposure time to reach that.

Now, the effect of background light interference is analyzed. Let us start with the strongest possible interference, direct sunlight, e.g., when the sun shines directly on the eye. It is known from solar photovoltaics technology that direct sunlight has an energy concentration of about 1 kW/m$^2$, and with a luminance of about 100,000 lux. In comparison, overcast and room lighting has about 1000 lux. It should be noted that lux is expressed in visible light, therefore infrared light contributes zero to lux, although it contributes toward energy concentration. Assume the eye region reflects about 10% of the direct sunlight, and the eye region is about 4 cm×4 cm=16 cm$^2$, and the reflected illumination power across the whole sun spectrum is 0.1*16*10$^{-4}$ m$^2$*1 kW/m$^2$=160 mW. If the only filter used is a general IR-passing filter, and assuming ¼ reflected sunlight can both pass and activate silicon-based photodiodes (note that the photon wavelength must be shorter than 1100 nm to activate silicon), and assuming the camera lens covers 1/1000 of a complete $2\pi$ stereo angle, the camera will receive a total of ¼*160 mW*1/1000=40 µW. Assuming the reflections are scattered and spread relatively uniformly among 100×100 pixels, then each pixel will receive 40 µW/10000=4 nW, at 0.1 A/W sensitivity, and will generate 0.4 nA or 400 pA of photo current as interference. This is 2.5 times as high as the photo current generated by the aforementioned LED. Since the sun is similar to a remote point light source, the reflections from the cornea will form a sun-induced glint, and that glint will be much stronger because the light is concentrated into a pixel. Note that if the background light interference is 1000 lux instead (e.g., room light), assuming the energy spectral distribution is similar to direct sunlight, then it will only generate 400 pA/100=4 pA, only 1/40 as high as the aforementioned LED-induced photo current. However, if the background light is a point source such as a light bulb, a glint may still be formed, and that glint may still cause sufficient interference to LED illumination.

Now, if a near infrared (NIR) narrow band (NB) filter is used that matches exactly with the output band produced by the LED, the effect of background light interference can be greatly reduced. For example, one datasheet (*Standard-Line Near Infra-red Bandpass Filter Listing*, Product 880.0 IF 40. www.cheshireoptical.com/NIRfilters.htm, which is incorporated herein by reference) shows that one such filter has a half width of 40 nm centered at 880 nm, with 65% transmission within the band, and 1000 to 10000-fold rejection ratio outside the band. Similarly, another datasheet (*MOLD LED Lamp L880 Series: Infrared LED Lamp*) shows that a certain NIR LED has a half width of 40 nm also centered at 880 nm. For simplicity, assuming the sunlight spectrum is relatively uniform from 300 nm to 1100 nm with a total bandwidth of 800 nm, and since out-of-band light is almost entirely rejected by the filter, then only 40 nm/800 nm=0.05 of background light will be within that narrow band, and roughly only 0.05*0.65=3.25% will pass through that filter. Now, for 100, 000 lux direct sunlight, the camera will receive only 0.0325*160 mW*1/1000=5.2 µW, and for scattered reflections, each pixel will get 5.2 µW/10000=0.52 nW, which in turn generates 52 pA of photo current as interference. Although it is not negligible, it is now much lower than the 160 pA that the LED generates. To be more accurate, with a 65% NIR NB filter the LED illumination will probably (assuming most LED illumination inside the 40 nm band) generate 0.65*160 pA=104 pA instead of 160 pA. For sun-induced glints, that will still be a problem, but that will be addressed in the next section. For room light at 1000 lux, even if the source (say light bulb) induces a glint, and the glint may be around 100 times stronger than scattered reflections, the source is also 100 times weaker than sunlight. Therefore, it is likely such a glint will not turn on the pMOSFET and cause noticeable interference.

To deal with sun-induced glints, we can perform two back-to-back exposures, so that they capture nearly identical eye features. In both exposures, we calibrate the exposure time to be the same as we would use without background light interference, e.g., it should cause a voltage drop slightly higher than Vth of the pMOSFET if only LED illumination is present. During the first exposure, we can turn off the LED, and check for the existence of any glints. If glints exist, they must be false glints, so their pixel locations are recorded. During the second exposure, the LED is turned on, and the detected glints are also recorded. Then, the pixel locations of false glints from the first exposure are compared against the glints in the second exposure, possibly with a small 2D neighborhood search window in case the glint has shifted its location slightly. Any glint from the second exposure that corresponds well (in terms of location proximity) to any false glint is deleted from the record. The remaining glint(s) are then most likely real glints induced by the LED. In one embodiment, the LED may be turned off during second exposure and turned on during first exposure, and false glints will be recorded during second exposure and compared against first exposure with effectively the same result, although such configuration is somewhat less streamlined and slightly less efficient. It should be known that if a false glint happens to overlap with a real glint, then the real glint will also be removed. Therefore, there is a small probability that the real glint is not detected during false glint removal. However, this may be alleviated by choosing from the 2 LEDs in the aforementioned embodiment the LED that is more unlikely to overlap with the false glints, based on the past history of real glints, false glints, and predicted locations of real glints from both LEDs. Of course, one can use and choose from more than 2 LEDs, but to lower the cost, 2 LEDs may be a good trade-off in terms of cost and performance.

Of course, higher LED power may also help with SNR. If the LED power is 10 times as strong as the aforementioned example, then only 1/10 of the exposure time is needed, and background light interference will be 1/10 as strong. One must note however, that LED power should be within limits set by health regulations in order to avoid any damage to the eye. A benefit of using higher LED power (and thus shorter exposure time) is that each exposure is less affected by rapid eye motions and that for double exposures they are more correlated to each other compared to lower LED power and longer exposure configurations.

In the above description, we turn LED illumination on and off in a time modulated manner, and while we do this we assume that background lighting is mostly constant over two exposures. This assumption is generally true of sunlight, incandescent light bulbs, candles, etc. But many devices, such as TV, CRT and LCD monitors have a known refresh rate, hence their display will also illuminate in a time modulated manner. To avoid background illumination changes during two exposures, one may occasionally turn off LED illumination for both exposures, and check whether the false glints are consistent between two exposures. If they are not consistent, it is likely that background lighting is time modulated, and actions may be taken accordingly. For example, the gaze tracker may choose a different time offset (but possibly maintaining the same tracking frequency) for two exposures during which background lighting is more stable. The gaze tracker may have to check the consistency and adjust the time offset on a periodic basis. The gaze tracker may employ algorithms to estimate the characteristics of time modulation so that it can compensate for the effect of background lighting more advantageously.

Modified APS with 2 Capacitors for Measuring the Voltage Difference Between Two Exposures In the above description, we already utilize time modulated (On/Off) LED illumination to identify false glints from real glints, and to carry it on further, we can perform two exposures and compare the voltage difference produced between the two exposures. In fact, this has been suggested before by a Jet Propulsion Laboratory article (See, for example, *Ambient-Light-Canceling Camera Using Subtraction of Frames*, NASA Tech Briefs, May 2004, which is incorporated herein by reference), where two images are taken, and subtraction is then performed in software between corresponding pixels on the two images. Zamir Recognition Systems (See, for example, published U.S. Patent Application No. 20080203277, which is incorporated herein by reference), has suggested a different design based more on hardware, where either a frequency-modulated signal and a frequency-passing filter is used, or a time-modulated (On/Off) signal is used, and a capacitor is charged and discharged in two exposures, respectively. The Zamir approach also proposes using 2 arrays of pixels, with each pixel having 1 capacitor, and subtracting the voltages of the two capacitors using a calculation module.

Figure 10:
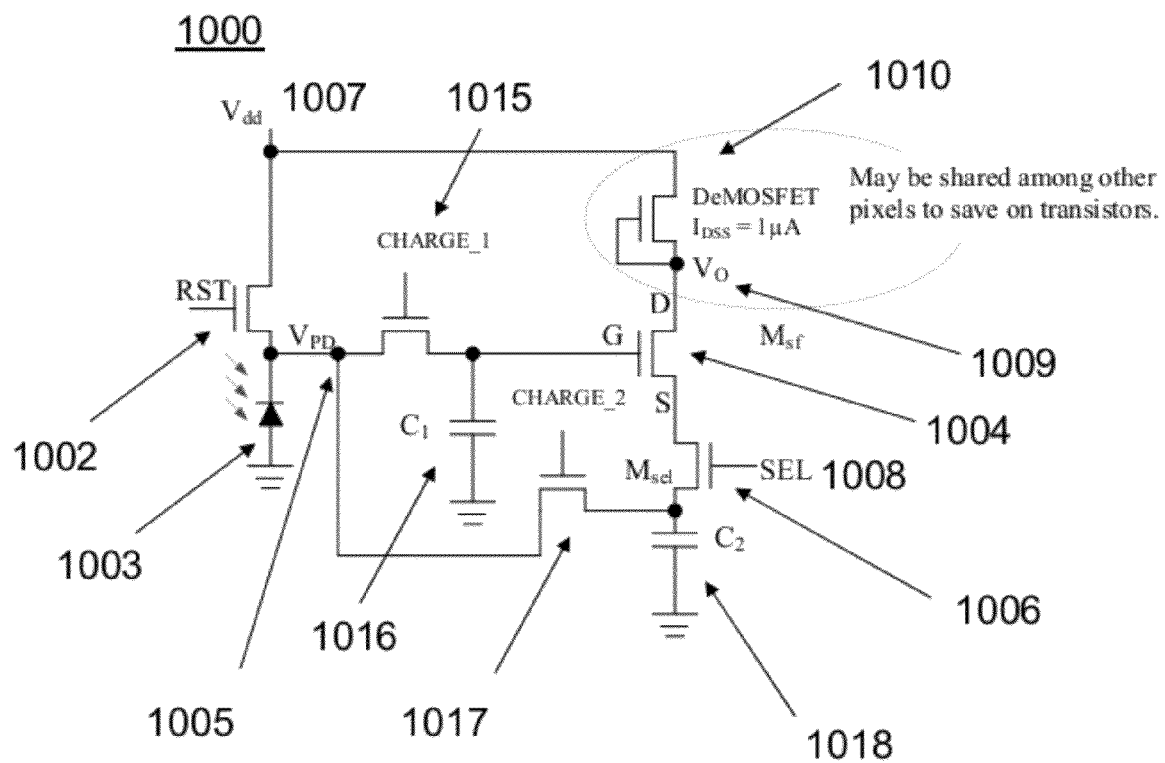
FIG. 10 shows a two-capacitor APS based voltage difference between two exposures, according to an embodiment of the present disclosure.

FIG. 10 shows a two-capacitor APS based voltage difference between two exposures, according to an embodiment of the present disclosure. APS 1000 includes reset transistor 1002, photodiode 1003, source-follower transistor 1004, photodiode voltage 1005, select transistor 1006, supply voltage 1007, select signal 1008, output voltage 1009, shared current limiting transistor 1010, first charging transistor 1015, first capacitor 1016, second charging transistor 1017, and second capacitor 1018. The proposed method of the present disclosure may also use time modulated illumination and subtraction, but instead of requiring 2 arrays of pixels with each pixel having 1 capacitor in Zamir approach, it utilizes 2 capacitors in 1 pixel and needs only 1 array of pixels. This can be seen in APS 1000. During the first exposure, the LED is off, and the first capacitor 1016 is charged by the photodiode 1003 (more precisely, the first capacitor 1016 is discharging because initially the voltage is Vdd−Vth, and the voltage will drop as photodiode 1003 gets light exposure). During the second exposure, the LED is on, and the second capacitor 1018 is charged by the photodiode 1003. The anode of the first capacitor 1016 is connected to the Gate of the Msf source-follower transistor 1004 (in one embodiment, an nMOSFET is used for the source-follower transistor 1004), and the anode of the second capacitor 1018 is connected to the Source of the source-follower transistor 1004 either indirectly as shown in FIG. 10, or directly by moving the select transistor 1006 to be beneath second capacitor 1018 with the same effect. With this configuration, if background lighting is stable during two exposures, and assuming that there is no over-exposure in both cycles, the voltage of the first capacitor 1016 will be higher than voltage of the second capacitor 1018, because the photodiode 1003 has more incident light due to LED illumination during the second exposure. The exposure time can be set to the same as when there is no background light interference. Therefore, the voltage difference will be slightly higher than Vth, and that will be enough to turn on the source-follower transistor 1004 and cause current to flow through it. For pixels that are not real glints, including false glints, and assuming no over-exposure, the voltage of first and second capacitors 1016 and 1018 will be almost the same, and the voltage difference will be close to 0V, and it will not be able to turn on the source-follower transistor 1004, even for false glints. In FIG. 10, two signals are used to control when to charge/discharge each capacitor. The "CHARGE_1" signal is sent to first charging transistor 1015 to control first capacitor 1016 and the "CHARGE_2" signal is sent to second charging transistor 1017 to control second capacitor 1018. Both CHARGE_1 and CHARGE_2 may be ON or high during the above-described corresponding reset and exposure modes, respectively.

In one embodiment, the transistors shown of APS 400, 500, 600, 700, 800, 900, and 1000 may be MOSFET transistors. In one embodiment, the transistors shown of APS 400, 500, 600, 700, 800, 900, and 1000 may be bipolar junction transistors. In one embodiment, the transistors shown of APS 400, 500, 600, 700, 800, 900, and 1000 may be more or less than the transistors that are shown.

Note that normally, MOSFETs are 3-terminal devices, with the substrate (bulk) shorted to a Source pin, which creates an implicit diode and makes the overall MOSFET susceptible to current flow whenever the Source voltage is higher than the Drain voltage for nMOSFETs. This problem may arise in FIG. 10, for example when capacitor 1 has a higher voltage than the photodiode and thus leaks charge into the photodiode. Swapping the Drain and Source pins does not solve this problem because then the photodiode may leak charge into capacitor 1.

In actual implementation, this issue can be avoided by making the Charge control MOSFETs effectively a 4-terminal device, where its substrates are not shorted to their Source pins. This is achieved via an often-used streamlined layout where a photodiode is seamlessly integrated with other MOSFETs, as shown in FIG. 11.

Figure 11:
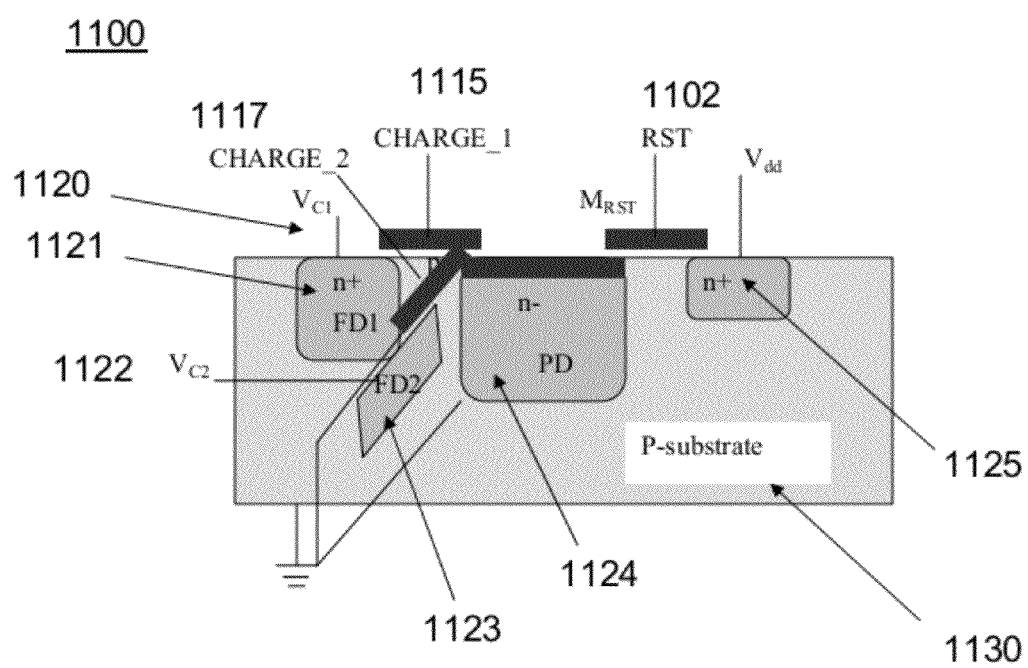
FIG. 11 shows a streamlined layout where a photodiode is seamlessly integrated with other MOSFETs, according to an embodiment of the present disclosure.

FIG. 11 shows a streamlined layout where a photodiode is seamlessly integrated with other MOSFETs, according to an embodiment of the present disclosure. Layout 1100 includes reset transistor 1102, first charging transistor 1115, second charging transistor 1117, VC1 voltage 1120 (which measures voltage of capacitor C1 which is made from first floating diffusion), first floating diffusion area and first n-well area 1121, VC2 voltage 1122 (which measures voltage of capacitor C2 which is made from second floating diffusion), second floating diffusion area 1123, photodiode n-well 1124, second n-well area 1125, and p-substrate 1130. Layout 1100 is a physical layout implementation of a photodiode 1003 shown in FIG. 10, for example, in order to avoid charge leakage. Note that the second capacitor 1018 is laid out in a 3D manner. FIG. 11 has some similarity with a 4T-APS which has a floating diffusion capacitor: one may refer to p. 40-41 and FIG. 2.23 of *Smart CMOS Image Sensors and Applications* for a comparison. Preferably, one should calibrate the manufacturing process and design the electrical potential profile of the CMOS image sensor chip such that the charge of the photodiode 1003 flows completely into the desired floating diffusion capacitor, to simplify calibration of the exposure time. Otherwise, charges will be shared somehow between the photodiode 1003 and the floating diffusion capacitor(s), and that generally complicates the calibration of exposure time.

With reference to FIG. 10, it should be noted that the above method has some element of dynamic circuit design, in that once Msf (or the source-follower transistor 1004) turns on and current starts flowing through it, the second capacitor 1018 will be gradually charged upward in terms of voltage, and once its voltage becomes as high as that of the first capacitor 1016, the source-follower transistor 1004 will turn off and current will stop flowing, and it would seem as if this pixel is not a glint, but that will only happen after the current flows for a long enough duration. Therefore, it is critical to sample the output voltage or current as quickly as possible before too much charging alters the output. For example, if the second capacitor 1018 has a capacitance of 1 pF, and if we use a current limiter of 1 μA, then it would take only 1 μs to alter (upward) its voltage by 1V. A Winner-Take-All (WTA) circuit (as seen in, for example, *A 200 μs Processing Time Smart Image Sensor for an Eye Tracker Using Pixel-Level Analog Image Processing*) can choose the winner output (from an entire row) strictly based on input magnitude (e.g., voltage depending on glint brightness), but has longer delay (typically in hundreds of ns) than CMOS logic (typically less than tens of ns), therefore, the WTA circuit is more likely to alter the glint pixels' capacitor 2's voltage. In addition, WTA has no memory, and to output all glint pixels in a row, several iterations are needed and they all cause the second capacitor 1018 in each pixel to be altered. Therefore, WTA is probably not as suitable for the proposed 2-capacitor APS, as shown in FIG. 10 by APS 1000. In comparison, with CMOS logic a row of latches or registers can be used to save the binary value of the APS output voltage in tens of ns, and after that, all APS elements can be turned off to both save power and to avoid the further altering of the voltage of the second capacitor 1018. Again, priority encoder circuits may be used to output all glint pixels in the current row, one at a time, and all of this can be done without turning on the source-follower transistor 1004 or altering the voltage of the second capacitor 1018 again.

It is also possible to use a pMOSFET for the 2-capacitor APS where the photodiode has a P-substrate. The anode of the second capacitor 1018 (expected to have a lower voltage for glint) may be connected to the Gate of a pMOSFET, and if the anode of first capacitor 1016 may be connected to the Source of pMOSFET, the Drain must be (indirectly) connected to Ground. Then, if the voltage of the second capacitor 1018 is lower than the voltage of the first capacitor 1016 by more than Vth, the pixel will turn on, the first capacitor 1016 will start to drain until it lowers to the voltage of the second capacitor 1018, and stops. So a similar dynamic circuit issue exists for pMOSFET based APS, and for the same reasoning before CMOS logic based latches/registers and priority encoder circuits are preferred over a WTA circuit for selecting glint pixels in the current row. For brevity, the exact circuit for a 2-capacitor APS with pMOSFET is omitted. Similarly, if the photodiode uses a N-substrate instead of a P-substrate, the circuit may also be adjusted accordingly to turn on the Msf only if the voltage of the second capacitor 1018 is sufficiently different from the voltage of the first capacitor 1016.

The uniqueness of the proposed method is that it combines the subtraction with the switching property of a MOSFET. However, this approach may add more complexity in design and manufacturing, therefore it should be used only if other methods don't perform well, e.g., if the false glints happen to overlap with real glints often. In practice, the simpler pMOSFET design with false glint removal is probably the better option in terms of complexity, practicality and cost. In all cases, a near infrared narrow band filter may be used to passively block out most of the background light interference.

With the 2-capacitor APS, its output voltage Vo (1009) may be sampled at the Drain of Msf or the source-follower transistor 1004. If it is not a glint pixel, Vo will be approximately equal to Vdd. If it is a glint pixel, Vo will be approximately VC2 (e.g., VC2 voltage 1122), the voltage of the second capacitor 1018, and it is not 0V. This creates an interface problem for CMOS logic, which usually assumes 0 and Vdd. In fact, if a middle voltage is used, it is likely both types of MOSFETs (recall that CMOS consists of both pMOSFETs and nMOSFETs) will turn on, breaking the assumption of only one type being turned on. This may cause CMOS logic to both malfunction as well as consume high power.

The solution to this interface problem is to use a different voltage supply for CMOS logic. During a reset, assuming a soft reset is used, VC2 will be initialized to the value of Vdd−Vth. After the 2nd exposure, even without background light interference, VC2 will drop at least by slightly more than Vth, say 1.25*Vth. Then, VC2 will drop to no more than Vdd−Vth−1.25*Vth=Vdd−2.25*Vth. Therefore, if we set the Ground voltage of CMOS logic to Vdd−2.25*Vth (instead of 0V), and its Full Power voltage to Vdd, the CMOS logic will interface with the APS output properly.

Note that in all the above analyses, for simplicity we assumed the same Vth value for all types of MOSFETs in the circuit. In practice, they need not be the same. By understanding the derivation of these analyses, one skilled in the art should be able to analyze the cases where Vth values are different.

The present disclosure provides a new type of eyeglasses fro myopia users, to relax and reduce eye strain, to slow down, stop and/or even reverse the progression of myopia. The low power gaze tracker is provided in this present disclosure that also implements eye and gaze tracking in general. A low cost, low power eye/gaze tracking solution in the form of eyeglasses may be provided. Some of the reasons why eye/gaze tracking may be considered non-trivial include head movement, background light interference, and reflections from eyeglasses, all of which may be greatly minimized in the proposed gaze tracker. Eyeglass reflection may no longer be a problem because the tracker is built into the eyeglasses. Eye/gaze tracking in and of itself has many applications in monitoring user behavior, such as tracking an item of focus while watching TV or seeing an advertisement on a billboard, for example, etc.

In the foregoing specification and the following appended documents, the disclosure has been described with reference to specific exemplary embodiments thereof. It will be evident that various modifications may be made thereto without departing from the broader spirit and scope as set forth in the following claims. The specification and drawings are, accordingly, to be regarded in an illustrative sense rather than a restrictive sense.

In this description, various functions and operations may be described as being performed by or caused by software code to simplify description. However, those skilled in the art will recognize that what is meant by such expressions is that the functions result from execution of the code/instructions by a processor, such as a microprocessor. Alternatively, or in combination, the functions and operations can be implemented using special purpose circuitry, with or without software instructions, such as using Application-Specific Integrated Circuit (ASIC) or Field-Programmable Gate Array (FPGA). Embodiments can be implemented using hardwired circuitry without software instructions, or in combination with software instructions. Thus, the techniques are limited neither to any specific combination of hardware circuitry and software, nor to any particular source for the instructions executed by the data processing system.

While some embodiments can be implemented in fully functioning computers and computer systems, various embodiments are capable of being distributed as a computing product in a variety of forms and are capable of being applied regardless of the particular type of machine or computer-readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

Routines executed to implement the embodiments may be implemented as part of an operating system or a specific application, component, program, object, module or sequence of instructions referred to as "computer programs." The computer programs typically include one or more instructions set at various times in various memory and storage devices in a computer, and that, when read and executed by one or more processors in a computer, cause the computer to perform operations necessary to execute elements involving the various aspects.

In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

A machine readable medium also can be used to store software and data which when executed by a data processing system causes the system to perform various methods. The executable software and data may be stored in various places including for example ROM, volatile RAM, non-volatile memory and/or cache. Portions of this software and/or data may be stored in any one of these storage devices. Further, the data and instructions can be obtained from centralized servers or peer to peer networks. Different portions of the data and instructions can be obtained from different centralized servers and/or peer to peer networks at different times and in different communication sessions or in a same communication session. The data and instructions can be obtained in entirety prior to the execution of the applications. Alternatively, portions of the data and instructions can be obtained dynamically, just in time, when needed for execution. Thus, it is not required that the data and instructions be on a machine readable medium in entirety at a particular instance of time.

Volatile RAM is typically implemented as dynamic RAM (DRAM) which requires power continually in order to refresh or maintain the data in the memory. Non-volatile memory is typically a magnetic hard drive, a magnetic optical drive, an optical drive (e.g., a DVD RAM), or other type of memory system which maintains data even after power is removed from the system. The non-volatile memory may also be a random access memory. The non-volatile memory can be a local device coupled directly to the rest of the components in the data processing system. A non-volatile memory that is remote from the system, such as a network storage device coupled to the data processing system through a network interface such as a modem or Ethernet interface, can also be used.

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., Compact Disk Read-Only Memory (CD ROMS), Digital Versatile Disks (DVDs), etc.), among others.

The computer-readable media may store the instructions. In general, a tangible machine readable medium includes any mechanism that provides (i.e., stores and/or transmits) information in a form accessible by a machine (e.g., a computer, network device, personal digital assistant, manufacturing tool, any device with a set of one or more processors, etc.).

In various embodiments, hardwired circuitry may be used in combination with software instructions to implement the techniques. Thus, the techniques are neither limited to any specific combination of hardware circuitry and software nor to any particular source for the instructions executed by the data processing system.

Although some of the drawings illustrate a number of operations in a particular order, operations which are not order dependent may be reordered and other operations may be combined or broken out. While some reordering or other groupings are specifically mentioned, others will be apparent to those of ordinary skill in the art and so do not present an exhaustive list of alternatives. Moreover, it should be recognized that the stages could be implemented in hardware, firmware, software or any combination thereof.

The disclosure includes methods and apparatuses which perform these methods, including data processing systems which perform these methods, and computer readable media containing instructions which when executed on data processing systems cause the systems to perform these methods.

While the methods and systems have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

In this regard it should be understood that for practical reasons and so as to avoid adding potentially hundreds of claims, the applicant has presented claims with initial dependencies only.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive forms so as to afford the applicant the broadest coverage legally permissible in accordance with the following claims.

In the foregoing specification, the disclosure has been described with reference to specific exemplary embodiments thereof. It will be evident that various modifications may be made thereto without departing from the broader spirit and scope as set forth in the following claims. The specification and drawings are, accordingly, to be regarded in an illustrative sense rather than a restrictive sense.

What is claimed is:

1. A low-power-consumption method of eye glint tracking in an electro-optical apparatus using an image sensor having active pixel sensors, comprising:
   determining, using a processor, whether image sensor pixels have a light exposure higher than a configured threshold;
   reporting said compared image sensor pixels by an image sensor circuit;
   for each of said active pixel sensors, turning on a MOSFET with a threshold voltage Vth if and only if its corresponding pixel has light exposure exceeding said configured threshold, and keeping said MOSFET turned off if its corresponding pixel's light exposure does not exceed said configured threshold;
   and
   using a latch or register circuit to hold on/off the result or state of the corresponding pixel.

2. The method of claim 1, wherein glint is generated by near infrared (NIR) illumination and using a NIR narrow band filter.

3. The method of claim 1, wherein said MOSFET has a corresponding photodiode, and if said photodiode is a P-substrate photodiode then said MOSFET is a pMOSFET, and if said photodiode is an N-substrate photodiode then said MOSFET is an nMOSFET.

4. The method of claim 3, wherein at least one NIR LED is used for glint tracking, and where two adjacent exposures are taken, with one exposure having the said LED Off, and the other exposure having the said LED On, where the glint candidates are filtered by the following steps:
   (1) Record locations of pixels that have their corresponding said MOSFET turned on during the exposure with the said LED Off, and mark them as false glint pixels;
   (2) Record locations of pixels that have their corresponding said MOSFET turned on during the exposure with the said LED On, and exclude those having location proximity to the false glint pixels from step (1) that is below a given distance threshold;
   (3) Cluster any remaining pixels from step (2) according to location proximity, and report the center of each cluster as a glint.

5. The method of claim 3, wherein an additional transistor is used to reduce Source voltage of said MOSFET from Vdd to Vdd-Vth, where Vdd is the positive supply voltage of the said additional transistor.

6. The method of claim 3, wherein a resistor or Depletion Enhancement MOSFET is used as load of Vo (output voltage) of the pixel.

7. The method of claim 3, wherein multiple columns of pixels on a row in a 2D array of pixels are accessed simultaneously, wherein a priority encoder or winner-take-all circuit is used to select the turned-on pixels one at a time.

8. The method of claim 1, wherein two capacitors are used to hold charges during two adjacent exposures, respectively, wherein a first exposure has a LED off and controls charges for a first capacitor, and a second exposure has the LED on and controls charges for a second capacitor, and a MOSFET's Gate pin is connected to an anode of the first capacitor, and its Source or Drain pin is connected to an anode of the second capacitor, wherein the MOSFET turns on if and only if LED illumination generates a voltage difference between two capacitors of greater than Vth.

9. The method of claim 8, wherein the MOSFET is an nMOSFET, and the Gate pin is connected to the said anode of the first capacitor, and Source pin is connected to the said anode of the second capacitor.

10. The method of claim 9, wherein a photodiode integrated with a reset transistor is further integrated with two charge control transistors, where each said charge control transistor connects a floating diffusion to the n-well area of the photodiode, in the form of a control gate.

11. The method of claim 8, wherein the MOSFET is a pMOSFET, and the Gate pin is connected to the said anode of the second capacitor, and Source pin is connected to the said anode of the first capacitor.

12. The method of claim 11, wherein the output voltage of the MOSFET is fed as input to CMOS logic circuit with Vss (ground)>Vdd−(k+1) Vth, where kVth is the expected voltage drop contributed by LED illumination and k>=1.

13. The method of claim 1, wherein a gate voltage of said MOSFET is the same as said MOSFET's corresponding pixel's photo-sensor voltage.

14. The method of claim 13, wherein glint is generated by near infrared (NIR) illumination and using a NIR narrow band filter.

15. The method of claim 13, wherein said MOSFET has a corresponding photodiode, and if said photodiode is a P-substrate photodiode then said MOSFET is a pMOSFET, and if said photodiode is an N-substrate photodiode then said MOSFET is an nMOSFET.

16. The method of claim 15, wherein an additional transistor is used to reduce Source voltage of said MOSFET from Vdd to Vdd-Vth, where Vdd is the positive supply voltage of the said additional transistor.

17. The method of claim 15, wherein a resistor or Depletion Enhancement MOSFET is used as load of Vo (output voltage) of the pixel.

18. The method of claim 15, wherein multiple columns of pixels on a row in a 2D array of pixels are accessed simultaneously, wherein a priority encoder or winner-take-all circuit is used to select the turned-on pixels one at a time.

* * * * *